US006716574B2

(12) United States Patent
Mathiesen et al.

(10) Patent No.: US 6,716,574 B2
(45) Date of Patent: Apr. 6, 2004

(54) OSP-C DERIVED PEPTIDE FRAGMENTS

(75) Inventors: Marianne Jartved Mathiesen, Hellerup (DK); Michael Theisen, Frederiksberg C (DK); Arne Holm, Holte (DK); Søren Østergaard, Copenhagen N (DK)

(73) Assignee: Dako A/S, Glostrup (DK)

( * ) Notice: Subject to any disclaimer, the term of this patent is extended or adjusted under 35 U.S.C. 154(b) by 32 days.

(21) Appl. No.: 09/974,992

(22) Filed: Oct. 10, 2001

(65) Prior Publication Data

US 2003/0138866 A1 Jul. 24, 2003

Related U.S. Application Data

(63) Continuation of application No. 09/180,089, filed as application No. PCT/DK97/00203 on May 2, 1997, now abandoned.

(30) Foreign Application Priority Data

May 2, 1996 (DK) .............................................. 0526/96

(51) Int. Cl.[7] ...................... G01N 33/53; G01N 33/567; G01N 33/554; G01N 33/569

(52) U.S. Cl. ............................ 435/4; 435/7.1; 435/7.2; 435/7.32; 435/7.92; 435/7.93; 435/7.94; 435/7.95

(58) Field of Search ............................. 435/4, 7.1, 7.2, 435/7.32, 7.92, 7.93, 7.94, 7.95

(56) References Cited

U.S. PATENT DOCUMENTS 6,509,019 B1 1/2003 Fuch et al.

FOREIGN PATENT DOCUMENTS

| | | | |
|---|---|---|---|
| EP | 0 522 560 | A2 | 1/1993 |
| EP | 0 506 868 | B1 | 7/1996 |
| WO | WO 91/09870 | | 7/1991 |
| WO | 9425596 | | 11/1994 |
| WO | WO 95/14781 | | 6/1995 |
| WO | 9535379 | | 12/1995 |

OTHER PUBLICATIONS

Parsons et al (*Peptide Hormones*; University Park Press, pp 1–7), Jun. 1976.*

Jobling et al (Mol. Microbiol. vol. 5 (7) pp 1755–1767), 1991.*

Vincent et al., Lyme Arthriitis Synovial γδ T Cells Respond to *Borrelia burgdorferi* Lipoproteins and Lipidated Hexapeptides, The American Association of Immunologists (1998).

Byers et al., Peptide Affinity and Concentration Affect the Sensitivity of M3–Restricted CTLs Induced In Vitro, The American Association of Immunologists (1999).

Wilske B. et al, "Medical Microbiology and Immunity", vol. 183 No. 1, 1994 pp. 43–59.

Brandt et al., "Key Epitopes on the ESAT–6 Antigen Recognized in Mice During the Recall of Protective Immunity to *Mycobacterium tuberculosis",* The Journal of Immunology, vol. 157, (1996) pp. 3527–3533.

Holm et al., "Multiple Column Peptide Synthesis", Peptides 1988, pp. 207–211.

Meldal et al., "Multiple column peptide synthesis, Part 2 (1,2)", Int. J. Peptide Protein Res., vol. 41 (1993) pp. 250–260.

Ulmer et al., "Polynucleotide vaccines", Curr. Opin. Invest. Drugs, vol. 2, No. 9 (1993) pp. 983–989.

Zweig et al., "Receiver–Operating Characteristic (ROC) Plots: A Fundamental Evaluation Tool in Clinical Medicine", Clinical Chemistry, vol. 39, No. 4 (1993) pp. 561–577.

Aguero–Rosenfeld et al., "Serodiagnosis in Early Lyme Disease", Journal of Clinical Microbiology, vol. 31, No. 12 (Dec. 1993) pp. 3090–3095.

Dressler et al., "Western Blotting in the Serodiagnosis of Lyme Disease", The Journal of Infectious Diseases, vol. 167 (Feb. 1993) pp. 392–400.

Jauris–Heipke et al., "Molecular Analysis of Genes Encoding Outer Surface Protein C (OspC) of *Borrelia burgdorferi* Sensu Lato: Relationship osp A Genotype and Evidence of Lateral Gene Exchange of ospC", Journal of Clinical Microbiology, vol. 33, No. 7 (Jul. 1995) pp. 1860–1866.

Livey et al., "Evidence for lateral transfer and recombination in OspC variation in Lyme disease Borrelia", Molecular Microbiology, vol. 18, No. 2 (1995) pp. 257–269.

Mathiesen et al., "Analysis of the human antibody response to outer surface protein C (OspC) of *Borrelia burgdorferi* sensu stricto, *B. garinii,* and *B. afzelii",* Med Microbiol Immunol, vol. 185 (1996) pp. 121–129.

Norman et al., "Serodiagnosis of Lyme Borreliosis by *Borrelia burgdorferi* Sensu Stricto, *B. garinii,* and *B. afzelii* Western Blots (Immunoblots)", Journal of Clinical Microbiology, vol. 34, No. 7 (Jul. 1996) pp. 1732–1738.

Theisen et al., "Evolution of the *Borrelia burgdorferi* Outer Surface Protein OspC", Journal of Bacteriology, vol. 177, No. 11 (Jun. 1995) pp. 3036–3044.

(List continued on next page.)

*Primary Examiner*—Mark Navarro
(74) *Attorney, Agent, or Firm*—Birch, Stewart, Kolasch & Birch, LLP

(57) ABSTRACT

A diagnostic method is disclosed which utilizes short C-terminal fragments of *Borrelia burgdorferi* sensu lato derived protein OspC. The 4 amino-terminal acids Pro-Lys-Pro (SEQ ID NO: 22) are shown to be essential in immune reactivity between sera from patients suffering from early borreliosis and various OspC derivatives and it is shown that in order to be effective as a diagnostic agent, 5 consecutive amino acid residues long homologue of a fragment identical to the 10 C-terminal amino acids of OspC (SEQ DI NO: 1). Also disclosed are vaccines utilizing the short peptides as well as methods for their preparation.

43 Claims, 6 Drawing Sheets

OTHER PUBLICATIONS

Figure 1:
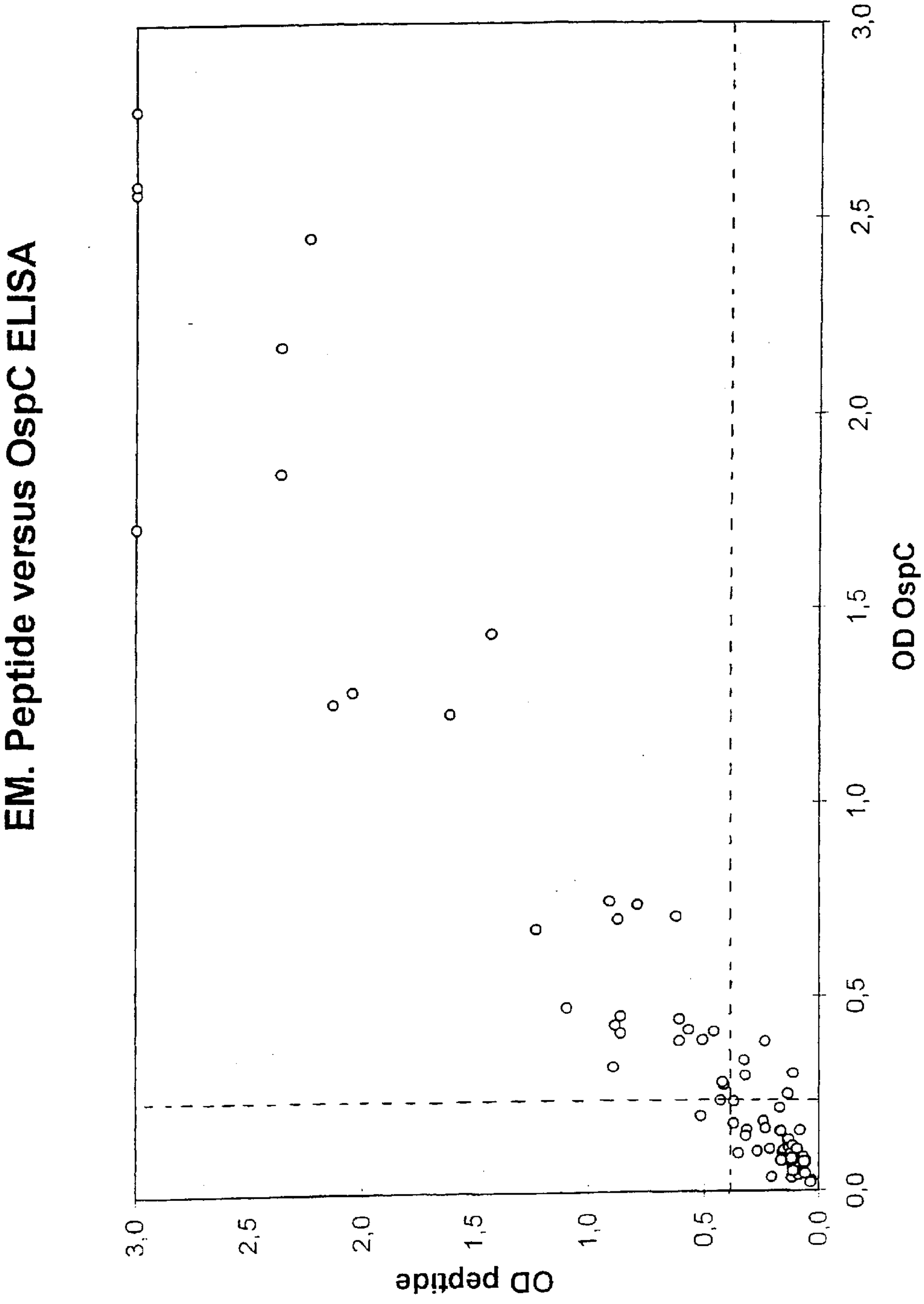

Theisen et al., "Polymorphism in ospC Gene of *Borrelia burgdorferi* and Immunoreactivity of OspC Protein: Implications for Taxonomy and for Use of OspC Protein as a Diagnostic Antigen", Journal of Clinical Microbiology, vol. 31, No. 10 (Oct. 1993) pp. 2570–2576.

Wilske et al., "Phenotypic Analysis of Outer Surface Protein C (OspC) of *Borrelia burgdorferi* Sensu Lato by Monoclonal Antibodies: Relationship to Genospecies and OspA Serotype", Journal of Clinical Microbiology, vol. 33, No. 1 (Jan. 1995) pp. 103–109.

Wilske et al., "Detection of IgM– and IgG Antibodies to *Borrelia burgdorferi* Using Different Strains as Antigen", Lyme Borreliosis II, Zbl. Bakt. Suppl. 18 (1989) pp. 299–309.

Wilske et al., "Immunological and Molecular Polymorphisms of OspC, an Immunodominant Major Outer Surface Protein of *Borrelia burgdorferi*", Infection and Immunity, vol. 51, No. 5 (May 1993) pp. 2182–2191.

Yu et al., "Multi–well ELISA based on independent peptide antigens for antibody capture Application to Lyme disease serodiagnosis", Journal of Immunological Methods, vol. 198 (1996) pp. 25–33.

Gerber et al., "Recombinant Outer Surface Protein C ELISA for the Diagnosis of Early Lyme Disease", The Journal of Infectious Diseases, vol. 171 (Mar. 1995) pp. 724–727.

Fung et al., "Humoral Immune Response to Outer Surface Protein C of *Borrelia burgdorferi* in Lyme Disease: Role of the Immunoglobulin M Response in the Serodiagnosis of Early Infection", Infection and Immunity, vol. 62, No. 8 (Aug. 1994) pp. 3213–3221.

Padula et al., "Use of Recombinant OspC from *Borrelia burgdorferi* for Serodiagnosis of Early Lyme Disease", Journal of Clinical Microbiology, vol. 32, No. 7 (Jul. 1994) pp. 1733–1738.

Padula et al., "Molecular Characterization and Expression of p23 (OspC) from a North American Strain of *Borrelia burgdorferi*", Infection and Immunity, vol. 61, No. 12 (Dec. 1993) pp. 5097–5105.

Wilske et al., "Recombinant immunoblot in the serodiagnosis of Lyme borreliosis", Medical Microbiology and Immunology, vol. 182 (1993) pp. 255–270.

Lebech et al., "Detection of *Borrelia burgdorferi* DNA in Urine Samples and Cerebrospinal Fluid Samples from Patients with Early and Late Lyme Neuroborreliosis by Polymerase Chain Reaction" Journal of Clinical Microbiology, vol. 30, No. 7 (Jul. 1992) pp. 1646–1653.

Hansen et al., "Improved Immunoglobulin M Serodiagnosis in Lyme Borreliosis by Using a u–Capture Enzyme–Linked Immunosorbent Assay with Biotinylated *Borrelia burgdorferi* Flagella", Journal of Clinical Microbiology, vol. 29, No. 1 (Jan. 1991) pp. 166–173.

Hansen et al., "Measurement of Antibodies to the *Borrelia burgdorferi* Flagellum Improves Serodiagnosis in Lyme Disease", Journal of Clinical Microbiology, vol. 26, No. 2 (Feb. 1988) pp. 338–346.

Dressler et al., "Antibody Responses to the Three Genomic Groups of *Borrelia burgdorferi* in European Lyme Borrealiosis", The Journal of Infectious Diseases, vol. 169 (Feb. 1994) pp. 318–318.

The QIA expressionist 2nd Edition, KEBO Lab/QIAGEN, Inc. (1992) pp. 42–43.

* cited by examiner

OSP-C DERIVED PEPTIDE FRAGMENTS

This application is a continuation application Ser. No. 09/180,089, now abandoned, filed on Dec. 22, 1998 and for which priority is claimed under 35 U.S.C. § 120. Application Ser. No. 09/180,089 is the national phase of PCT International Application No. PCT/DK97/00203 filed on May 2, 1997 under 35 U.S.C. § 371. The entire contents of each of the above-identified applications are hereby incorporated by reference. This application also claims priority of Application No. 0526/96 filed in Denmark on May 2, 1996 under 35 U.S.C. § 119.

FIELD OF THE INVENTION

The present invention relates to a novel method for the diagnosis of Lyme borreliosis, or more specifically a method for detecting antibodies directed against the OspC protein of *Borrelia burgdorferi* sensu lato. Further, the invention pertains to an immunological agent which comprises a specific peptide fragment derived from the C-terminus of OspC and uses of this immunological agent in the diagnosis of Lyme borreliosis as well as for vaccination purposes. The invention finally relates to novel polypeptide fragments derived from the C-terminus of OspC as well as to short peptides derived from this region.

BACKGROUND OF THE INVENTION

The tickborne spirochaete *Borrelia burgdorferi* is the etiological agent of Lyme borreliosis, which is at present the most common vector-borne human disease in Europe and North America. Lyme borreliosis is a common tick-borne disease which is caused by one of the three genospecies of *B. burgdorferi* sensu lato: *B. burgdorferi* sensu stricto, *B. garinii*, and *B. afzelii*. The clinical manifestations are diverse and may involve the skin, central nervous system, heart, and joints. The symptomatology can be divided into three stages: The first stage: skin lesion; the second stage: meningitis, arthritis, and myocarditis; the third stage: chronic meningitis, chronic arthritis, and chronic skin lesion.

It is desirable to have access to an assay with a high diagnostic sensitivity already in the first stage of Lyme borreliosis, in order to diagnose and treat patients before they develop severe symptoms of the later stages of Lyme borreliosis.

Laboratory diagnosis of Lyme borreliosis has been possible since the discovery of *B. burgdorferi* in 1982. However, the ultimate diagnostic assay has not yet been developed. Laboratory confirmation of Lyme borreliosis still relies mainly on the detection of antibodies to *B. burgdorferi*. Assays based on whole cell *B. burgdorferi* extracts lack diagnostic specificity due to antibodies cross-reacting with antigens from a wide range of bacterial species. Western blotting (WB) has proved difficult to perform due to strain differences, the complexity of the band patterns, and inherent problems in standardization of Western blotting in general. Efforts have therefore mainly been directed towards identification of single immunodominant antigens, either in the native form or as recombinant proteins, which can be purified and used as test antigens.

According to Western blot studies there are only two *B. burgdorferi* antigens that meet the essential criterium of eliciting an early and strong antibody response in the majority of patients. These are the *B. burgdorferi* flagellum and the outer surface protein C (OspC). Whereas the performance of EIA's using purified native *B. burgdorferi* flagellum is well documented, the reported experience with OspC EIA's is still limited.

Other routes to the specific diagnosis of Lyme borreliosis have been suggested. A fraction of membrane related proteins and lipids known as "fraction B" disclosed in EP-A-445,135 has been demonstrated to exhibit an improved diagnostic specificity, but the provision of fraction B requires that *Borrelia burgdorferi* sensu lato is cultured and subsequently treated in a series of steps.

A high prevalence of IgM anti-OspC antibodies has been found in patients in the two first stages of Lyme borreliosis by means of Western blotting, using native and recombinant OspC (rOspC) and by means of ELISA, using rOspC (Fung B. P. et al. (1994); Gerber M. A. et al. (1995); Wilske B. et al. (1994); Padula S. J. et al. (1994)).

SUMMARY OF THE INVENTION

In general, it has been concluded by the present inventors that the sensitivity of diagnosis of the early stages of Lyme borreliosis could be increased by combining the results from an immunoassay based on the detection of anti OspC antibodies and the results from the current available immunoassays for the flagellum.

More specifically, the present inventors have reached the conclusions that certain C-terminal fragments of OspC comprise an epitope which is essential in the human immune system's recognition of OspC. Additionally, it has been found that the serodiagnostic sensitivity of said C-terminal fragments is surprisingly high when compared to that of full-length OspC.

These conclusions have been reached after immunological experiments which surprisingly have revealed that 1) a synthetic peptide derived from the C-terminus of OspC of *B. burgdorferi* sensu lato exhibits an immunological sensitivity in detecting sera from human Lyme borreliosis patients which is at least 85% of the sensitivity of full length recombinant *B. burgdorferi* sensu lato derived OspC ($rOspC_{fl}$) when used in similar assays, and 2) a recombinant *B. burgdorferi* sensu lato OspC truncate which lacks the 7 carboxyterminal amino acids ($rOspC_t$) exhibits, when compared to full length recombinant OspC ($rOspC_{fl}$), a very poor, if any, immunological reactivity with sera from patients suffering from Lyme borreliosis.

These immunological experiments were part of scientific work which aimed at producing an immunoassay based on recognition by antisera of recombinant OspC. However, in the first attempt, a diagnostic sensitivity of less than 5% was achieved in early stage of Lyme borreliosis (this involves the first and second stage of Lyme borreliosis), cf. Example 1. Here, the deduced amino acid sequence of three OspC proteins representing each of three *B. burgdorferi* genospecies (*B. burgdorferi* sensu stricto, *B. garinii*, and *B. afzelii*) were used as test antigens. However, the recombinant proteins all lacked the seven C-terminal amino acid residues, because these had not yet been determined for the three pertinent isolates of *Borrelia burgdorferi* sensu lato.

In the second attempt the entire recombinant OspC proteins ($rOspc_{fl}$) from all three strains were produced, including the last seven amino acid residues, which had then been deduced. Further, the deduced amino acid sequence in the C-terminus of the OspC protein was identical for the genospecies of *B. garinii* and *B. afzelii* used in the first attempt, whereas the *B. burgdorferi* sensu stricto genospecies had a valine residue instead of an alanine residue in position 205. By employing the $rOspC_{fl}$ proteins as test antigens in an ELISA, diagnostic sensitivities were achieved of 44% for IgM in the first stage of Lyme borreliosis and 48% for IgM in the second stage of Lyme borreliosis in a set of preliminary tests. The diagnostic sensitivity for borreliosis was identical for all three genospecies. Therefore, a more comprehensive testing of the immunological reactivity of $rOspC_{fl}$ and of synthetic C-terminus derived peptides were performed, cf. Example 2.

On the background of these findings, it was concluded that the seven carboxy-terminal amino acid residues comprise, constitute, or form part of an antigenic epitope which is essential in the human immunological recognition of OspC and it was therefore conceived that this epitopic region can be the basis for novel and improved diagnostic means.

It was further investigated to what degree each of the single amino acids contributes to the immune reactivity of the C-terminus of OspC, and it was found that the last 5 amino acids can only be varied to a very limited degree, whereas e.g. alanine substitutions in other amino acids in the C-terminus had no or little impact on immune reactivity.

A number of advantages can be provided by using short OspC fragments as part of an immunological agent in the diagnosis of early stage Lyme borreliosis. Most important, an immunoassay, such as an ELISA, which is based on a synthetic peptide—as opposed to using full-length or near-full-length OspC—simplifies the preparation and purification steps of the components of the assay and thus helps standardize the assay.

Further, the use of a short peptide in an immunoassay may lead to a decrease in the cross-reactivity with antibodies raised against other antigens as a consequence of the abolishment of a large number of potentially cross-reacting epitopes in OspC (for instance, the present peptides lack sequence homology with the variable membrane proteins of *B. Hermsii*). On the other hand, the use of an antigen, such as full-length OspC, which comprises a significant number of epitopes normally has as a result that the signal from a cross-reacting epitope may be "drowned" in the signals from other epitopes, an effect which cannot be expected from an antigen comprising only a few epitopes. Therefore, the short peptide should preferably exhibit a very specific pattern of immunological reaction with antibodies against other antigens, cf. the discussion of specificity below.

As test antigen in an immunoassay, the peptide of the invention may prove to exhibit a superior diagnostic sensitivity in the early stage of Lyme borreliosis compared to e.g. an $rOspC_{fl}$ ELISA. This is due to the fact that the relatively small size of the peptide of the invention allows binding of a large number of peptides to the solid surface of the ELISA without the side effect that these peptides interfere with each other, whereas the relatively large $rOspC_{fl}$ molecules may indeed interfere with themselves and each other and e.g. mask epitopes which could potentially react with antibodies.

Finally, even though it would be expected that the use of a short peptide would lead to a marked decrease in sensitivity when testing patient antisera (which by nature are polyclonal), the present inventors have demonstrated that short peptides exhibit a high sensitivity when compared to the $rOspC_{fl}$ (cf. Example 2).

Therefore, peptide fragments derived from the C-terminus of *Borrelia burgdorferi* sensu lato OspC will according to the invention serve as diagnostic tools in the diagnosis of Lyme borreliosis.

In its broadest aspect, the invention therefore relates to a method for determining previous or ongoing sensitization of a subject with OspC polypeptide of *Borrelia burgdorferi* sensu lato, said method comprising contacting immunoglobulins or T-cells derived from the subject with at least one immunological agent comprising a polypeptide fragment which contains a peptide having a degree of sequence identity of at least 50% with a *Borrelia burgdorferi* sensu lato derived peptide which either has the amino acid sequence SEQ ID NO: 1:

Pro-Val-Val-Ala-Glu-Ser-Pro-Lys-Lys-Pro or has a subsequence of SEQ ID NO: 1 which has a length of at least 5 amino acid residues, and subsequently detecting the degree, if any, of immunological reactivity between the immunoglobulins and the immunological agent or between the T-cells and the immunological agent, a significant immunological reaction being indicative of previous sensitization with OspC polypeptide from *Borrelia burgdorferi* sensu lato, in which method said polypeptide fragment a) is one which, when used in a first ELISA (the "peptide ELISA" described in the Example section), results in an immunological average sensitivity in detecting randomly selected antisera from patients suffering from early stage Lyme borreliosis which is at least 75% of the average immunological sensitivity in detecting the same antisera in a second ELISA (the "rOspC ELISA" described in the Example section) using full-length recombinant OspC derived from *Borrelia garinii*, and/or b) has a length of at most 60 amino acid residues.

(In short, the first ELISA can be performed as follows:

i) coating flat-bottom microdilution plates with 100 μl of streptavidin (2.5 μg/ml) in citrate buffer (pH 5) and incubating overnight at 4° C., ii) washing the plates four times for one minute with phosphate buffered saline (PBS) containing 0.5 M NaCl and 0.1% (vol/vol) Tween 20 (pH 7.2), iii) adding to each well 100 μl of biotinylated polypeptide fragment which is prodiluted in PBS containing 0.37 M NaCl, 0.5% (vol/vol) Tween 20, and 1% (wt/vol) milkpowder (pH 7.0)) and incubating the plates overnight at 4° C., iv) washing the plates four times for one minute with PBS containing 0.5 M NaCl and 0.1% (vol/vol) Tween 20 (pH 7.2), v) adding 100 μl of serum diluted 1:200 in PBS containing 0.7 M NaCl, 0.1% (vol/vol) Tween 20, and 1% (wt/vol) milkpowder (pH 7, 2) to each well and incubating for 2 hours at 20° C. on a rocker platform, vi) washing the plates four times for one minute with PBS containing 0.5 M NaCl and 0.1% (vol/vol) Tween 20 (pH 7.2), vii) adding 100 μl of peroxidase conjugated rabbit anti-human IgM diluted 1:1000 in PBS containing 0.5% Tween 20 and 1% milkpowder (pH 7.4) to each well and incubating for 1 h at 20° C., viii) washing the plates four times for one minute with PBS containing 0.5 M NaCl and 0.1% (vol/vol) Tween 20 (pH 7.2), ix) adding 200 μl of o-phenylenediamine (0.33 mg/ml) dissolved in citrate buffer (pH 5) with 0.04% (vol/vol) $H_2O_2$ to each well and protecting the plates from light for 15 minutes, x) stopping the enzymatic reaction by adding 50 μl of 3 M $H_2SO_4$ to each well, xi) reading the optical density (OD) at 492 nm for each well, xii) if two OD values the same serum sample differs more than 10% from the mean, retesting said sera samples by steps i-xi, and xiii) establishing as a result that an OD of at least 0.460 is a significant immunological reaction whereas an OD of less than 0.460 is a negative reaction;

similarly, the second ELISA can be performed as follows:

I) coating flat-bottom microdilution plates with 100 μl of an optimum coating concentration of full length rOspC ($rOspC_{fl}$), diluted in 0.05 M bicarbonate pH 9.6, for 1 hour at 20° C. on a rocker platform and thereafter overnight at 4° C.

II) washing the plates four times for one minute with phosphate buffered saline (PBS) containing 0.5 M NaCl and 0.1% (vol/vol) Tween 20 (pH 7.2), III) blocking unspecific protein binding with 100 μl 3% (wt/vol) milk powder in PBS for 1 hour, IV) washing the plates four times for one minute with PBS containing 0.5 M NaCl and 0.1% (vol/vol) Tween 20 (pH 7.2), V) adding 100 μl of serum diluted 1:200 in PBS containing 0.1% (vol/vol) Tween 20, 0.02% $NaN_3$ and 1% (wt/vol) milk powder to each well and incubating for 2 hours at 20° C., VI) washing the plates four times for one minute with PBS containing 0.5 M NaCl and 0.1% (vol/vol) Tween 20 (pH 7.2), VII) adding 100 μl of peroxidase conjugated rabbit anti-human IgM diluted 1:1000 in PBS containing 0.5% Tween 20 and 1% milkpowder (pH 7.4) to each well and incubating for 1 h at 20° C., VIII) washing the plates four times for one minute with PBS containing 0.5 M NaCl and 0.1% (vol/vol) Tween 20 (pH 7.2), IX) adding 200 μl of o-phenylenediamine (0.41 mg/ml) dissolved in citrate buffer (pH 5) with 0.04% (vol/vol) $H_2O_2$ to each well and protecting the plates from light for 15 minutes, X) stopping the enzymatic reaction by adding 50 μl of 3 M $H_2SO_4$ to each well, XI) reading the optical density (OD) at 492 nm for each well, XII) if two OD values the same serum sample differs more than 10% from the mean, retesting said sera samples by steps i-xi, and XII) establishing as a result that an OD of at least 0.230 is a significant immunological reaction whereas an OD of less than 0.230 is a negative reaction.)

In conclusion, the present invention thus provides short (normally synthetic) peptides which bind anti-Borrelia antibodies in serum from patients with early stage Lyme borreliosis. These peptides can be used together with different means enabling the easy detection of *Borrelia burgdorferi* sensu lato infection. A serodiagnostic assay based on the use of these peptides, optionally combined with other antigens of *B. burgdorferi* increases the total diagnostic sensitivity. Accordingly the patients can be treated before they develop symptoms in the central nervous system.

DETAILED DESCRIPTION OF THE INVENTION

The immunological agent of the invention exhibits a surprisingly high sensitivity in detecting Borrelia antibodies in sera from patients with Lyme borreliosis. The sensitivity of anti-borrelia immunoassays can therefore be increased and this represents an important advance in the ability to detect the disease in an early stage.

In the following, a number of terms will be explained in greater detail.

By the term "immunological agent" is herein meant a chemical entity which is capable of reacting with antibodies raised against a C-terminal epitope of OspC polypeptide of *Borrelia burgdorferi* sensu lato. The agent comprises a polypeptide fragment containing the above-defined peptide, but may also contain other features such as linkers and labels, cf. the discussion below.

The term "polypeptide fragment" does in the present context mean a peptide, oligopeptide or polypeptide which normally may form part of a protein, whereas a "peptide" herein is a polypeptide fragment having a length of at most 10 amino acid residues.

The term "degree of sequence identity" means the percentage of matching amino acid residues (with respect to both position and type) in the peptide of the invention and an aligned peptide of equal length and by the term "subsequence" is herein meant a consecutive stretch of amino acid residues taken from SEQ ID NO: 1. There are 20 specific subsequences of SEQ ID NO: 1 which have a length of at least 5 amino acids.

By the term "immunological reactivity" is herein meant the degree of immunological binding between an antigen and an antibody (as measured by an immunoassay) or the degree of T-cell reactivity elicited by contacting an antigen with a T-cell (measured as a proliferative response or a cytokine release).

An "immunoglobulin" is a naturally occurring antibody taken from the classes IgM, IgG, IgA, IgE and IgD.

The term "sensitivity" as used herein, is defined as the ability of a method of the invention to detect antibodies against the OspC antigen in a sample from an individual with clinically diagnosed Lyme borreliosis. The sensitivity is mathematically defined as $$\frac{p_{meas}}{p_{true}} 1,$$

wherein $p_{meas}$ is the number of positives found by the test and $p_{true}$ is the total number samples tested (samples taken from individuals all diagnosed clinically).

When used herein, the related term "specificity" refers to the ability of a method to avoid producing false-positive results or signals, i.e. to avoid giving a positive signal for the presence of anti-OspC antibodies when these are in fact absent. It will be understood that a method producing a low rate of false-positive results or signals is a method with a high degree of specificity. The specificity of a test is defined as $$\frac{n_{meas}}{n_{true}} 2,$$

wherein $n_{meas}$ is the number of true negative samples measured in the test and $n_{true}$ is the total number of persons not affected with the disease.

In this context the term "signal" thus refers to the measurable output of an assay testing for the presence of anti-OspC antibodies. In an ELISA, the signal is normally the optical density (OD), which can be defined as $$OD = \log\frac{1}{1-A} 3,$$

wherein "A" is the relative absorption of light (ranging between 0 and 1), which is corrected for a blind standard.

In the present context the term "cut-off value" refers to the minimal signal from an assay which is regarded as a positive signal. Therefore, apart from the immunological nature of the antigen used as probe in a given immunoassay, also the cut-off value used in the assay has an impact on the sensitivity and specificity of an assay. If e.g. the cut-off value is set to a very low value of the measured parameter (e.g. the OD), the sensitivity of the assay will approximate 1 but on the expense of specificity which will be close to zero, since almost all true negatives will be deemed positive in the assay and hence $n_{meas}$ will approximate zero.

It will therefore be understood that the efficacy of a given immunoassay is highly dependent on the cutoff-value and that the determination of the cutoff-value further is dependent on the intended use of the assay. Of course, the normal situation is that an assay should be both sensitive and specific, but under some circumstances this need not be imperative. This can e.g. be the case in situations where a sensitive screening assay is used to narrow the "field of search" and one or more specific verification assay(s) is/are used to verify the result of the screening assay. In this situation, the first screening assay need not be very specific, and accordingly the verification assay need not be very sensitive if the verification step, taken as a whole, has the same sensitivity as the screening assay. As a practical matter, in the experiments performed utilising the ELISA techniques reported herein the cut-off value has been defined as the optical density which excludes 98% of sera from healthy blood donors. In other words, in the present context, the chosen cut-off value is expected to result in 2% false-positive signals derived from healthy and non-sensitized individuals. In practice, sera from 100 randomly chosen blood donors were subjected to the two ELISAs described in the examples and optical densities were measured. The cutoff-value was defined as the third OD in descending order, i.e. the third-highest measured value.

Accordingly, in the present context the term "positive signal" (also called "a significant immunological reaction"), i.e. a final or presumptive result which states that the sample contains anti-OspC antibodies, denotes a signal above the chosen cut-off value and the term "negative signal" (or "negative reaction"), i.e. a final or presumptive result which states that the sample does not contain anti-OspC antibodies, denotes a signal below the cut-off value.

A "true-positive" signal or result is herein defined as a positive signal or result which can be confirmed clinically by means of other available diagnostic tools and a "true negative signal" is hence a negative signal which does not give rise to a positive result when using other available diagnostic tools.

Consequently, a "false-positive" signal or result is defined herein as a positive signal or result which cannot be confirmed, a "false-negative" signal or result is defined as a negative signal or result which cannot be confirmed as negative.

Apart from the cutoff-value in a given assay, the precise scenario wherein the assay is used may have an impact on the specificity. It might very well be that an immunoassay is not specific if tested against a wide variety of random samples, but the assay may nevertheless be regarded as specific "in practice", since the cross-reacting samples are representative of material which from a clinical point of view will never be tested.

It is expected that the method of the present invention when fine-tuned will result in an even higher sensitivity than methods employing full-length OspC. As demonstrated in the examples, in the early stages (1 and 2) of Lyme borreliosis, the optical densities determined in an ELISA using a peptide fragment of the present invention are markedly higher than OD's determined in an ELISA using full-length OspC.

According to the invention, the peptide which is used in the inventive method is a homologue of the *Borrelia burgdorferi* sensu lato derived peptide having the amino acid SEQ ID NO: 1 or of a subsequence of SEQ ID NO: 1 of at least 5 amino acid residues, and the homology is in the form of at least 50% sequence identity with SEQ ID NO: 1, cf. the above. It is preferred, however, that the degree of sequence identity with SEQ ID NO: 1 (or its subsequences) is at least 60%, but even higher percentage limits, i.e. 70%, 80%, and 90%, are more preferred, since it is expected that the optimum immunological reactivity of the peptide is obtained when it resembles SEQ ID NO: 1 (or its subsequences) to the highest extent. Therefore, the most preferred sequence identity between the peptide of the invention and SEQ ID NO: 1 (or its subsequences) is 100%.

The length of the peptide of the invention is, when it is in the form of a homologue of a subsequence of the *Borrelia burgdorferi* sensu lato derived peptide, according to the invention, at least 5 amino acid residues, since this is the minimum length of a linear epitope. In this context it should also be noted that Example 3 herein demonstrates the importance of the last 5 C-terminal amino acid residues of SEQ ID NO: 1 for the immune reactivity against OspC positive sera (in fact, even the last 4 amino acids of OspC are capable of interfering with the binding between rOspC and some antisera).

According to the invention the length of the subsequence can also be at least 6, preferably at least 7, and more preferably 8 amino acid residues in order to maintain a high specificity in immune reactivity. In the most preferred embodiments, the subsequence is of at least 9 amino acid residues length. In a most preferred embodiment, the *Borrelia burgdorferi* sensu lato derived peptide has the amino acid sequence SEQ ID NO: 1, since a peptide of this length has experimentally proven to be effective as a diagnostic means in a large scale experiment. It is, however, expected that shorter peptides will prove equally effective in such assays and the most preferred peptides of the invention have a length of between 5 and 10 amino acid residues (i.e. 5, 6, 7, 8, 9 or 10 amino acid residues).

As can be seen from the examples, the inventors have shown that the seven carboxyterminal amino acids of OspC are essential in the humeral immune response by humans against full length OspC. Therefore, these seven amino acids either comprise or form part of an essential epitope, and consequently at least 2 consecutive amino acids of this 7 amino acid stretch should form part of the peptide used in the inventive method. It has further been shown that the last 4 amino acids are quasi-essential for immune reactivity of short OspC derived peptides and therefore it is especially preferred that the *Borrelia burgdorferi* sensu lato derived peptide serving as "template" for the peptide of the invention comprises these 4 amino acids. Hence, it is preferred that the peptide of the invention includes a 5 amino acid residues long C-terminus which has a degree of sequence identity of at least 60% (preferably at least 80% and most preferably a total identity) with the 5 C-terminal amino acid sequence of SEQ ID NO: 1. It is especially preferred that the peptide of the invention includes the amino acid sequence -Pro-Lys-Lys-Pro-COOH in the C-terminus.

Hence, according to the invention, the subsequence of the *Borrelia burgdorferi* sensu lato derived peptide preferably includes at least 4 of these 7 carboxyterminal amino acid residues of SEQ ID NO: 1, but higher degrees of conservation are preferred, i.e. the subsequence may include 5, 6 or even all 7 carboxyterminal amino acids in SEQ ID NO: 1.

Even though it is expected that the peptide used in the inventive method should have a high degree of resemblance with SEQ ID NO: 1, it is reasonable to assume that the peptide's specificity and sensitivity as a diagnostic tool can be enhanced by modifying the amino acid sequence of the peptide. The amino acid of the peptide can be expressed by the general formula I:

$$A^{10}\text{-}A^{9}\text{-}A^{8}\text{-}A^{7}\text{-}A^{6}\text{-}A^{5}\text{-}A^{4}\text{-}A^{3}\text{-}A^{2}\text{-}A^{1} \qquad \text{I}$$

(which of course fulfil the above criteria) and wherein

- $A^1$, and $A^4$, independently from each other, designate residues of an amino acid, wherein a nitrogen atom capable of forming part of a peptide bond is part of a ring structure;
- $A^2$ and $A^3$, independently from each other, designate residues of a positively charged or polar amino acid;
- $A^5$, $A^6$, $A^7$, $A^8$, $A^9$ and $A^{10}$, independently from each other, are absent or designate residues of any amino acid, but preferably selected from the group consisting of alanine, arginine, asparagine, aspartic acid, cysteine, cystine, glycine, glutamic acid, glutamine, histidine, isoleucine, leucine, lysine, methionine, phenylalanine, proline, serine, threonine, tryptophan, tyrosine, valine, 2-aminoadipic acid, 3-aminoadipic acid, beta-alanine, 2-aminobutyric acid, piperidinic acid, 6-aminocaproic acid, 2-aminoheptanoic acid, 2-aminoisobutyric acid, 3-aminoisobutyric acid, 2-aminopimelic acid, 2,4-diaminobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, N-methyliso-leucine, 6-N-methyllysine, N-methylvaline, norvaline, norleucine, 6-aminohexanoic acid, L-thiazolidine-4-carboxylic acid, and ornithine.

It is preferred that the amino acids, which are used as substituents in SEQ ID NO: 1 in order to produce the peptide used in the inventive method, closely resembles the amino acids which are present in the carboxyterminus of naturally occurring variant of native OspC. At present, the inventors are aware of the following naturally occurring variations in the C-terminus of OspC (based i.a. on the disclosures in WO 94/25596): $A^{10}$ can be proline (a hydrophobic amino acid), $A^9$ can be valine or isoleucine (both hydrophobic amino acids), $A^8$ can be valine (hydrophobic), $A^7$ can be alanine, valine, threonine and serine (hydrophobic and polar, i.e. non-charged), $A^6$ can be glutamic acid (a negatively charged amino acid), $A^5$ can be serine, threonine, asparagine and alanine (all uncharged amino acids), $A^4$ and $A^1$ can be proline (wherein the nitrogen atom forming part of the peptide bond is part of a ring structure), $A^3$ can be lysine (positively charged), and $A^2$ can be lysine (positively charged) and asparagine (polar). Further, as demonstrated in Example 3 herein, the substitution of any of $A^5$ to $A^{10}$ with alanine (or with phenylalanine for $A^7$) has no influence on the immune reactivity between OspC positive sera and the decapeptide having SEQ ID NO: 1 (when substituted).

In the present context, the term "hydrophobic amino acid" is intended to include the naturally occurring L-amino acids alanine, valine, leucine, isoleucine, proline, methionine, phenylalanine, and tryptophan, as well as other non-naturally occurring or unusual amino acids (including D-forms) which are non-polar at pH 7.

The term "polar amino acid" is intended to include the naturally occurring L-amino acids glycine, serine threonine, cysteine, tyrosine, asparagine, and glutamine as well as other non-naturally occurring or unusual amino acids (including D-forms) which are polar but uncharged at pH 7.

The term "negatively charged amino acid" is intended to include the naturally occurring L-amino acids aspartic acid and glutamic acid as well as other non-naturally occurring or unusual amino acids (including D-forms) which carry a net negative charge at pH 7.

The term "positively charged amino acid" is intended to include within its scope the naturally occurring L-amino acids lysine, arginine and histidine, as well as other non-naturally occurring or unusual amino acids (including D-forms) which carry a net positive charge at pH 7.

Hence it is preferred that the substituents $A^5$–$A^{10}$ in the formula I are defined as follows:

- $A^5$ is absent or designates a residue of a non-charged amino acid;
- $A^6$ is absent or designates a residue of a negatively charged amino acid;
- $A^7$ is absent or designates a residue of a hydrophobic or polar amino acid; and
- $A^8$, $A^9$, and $A^{10}$ independently from each other, are absent or designate a residue of a hydrophobic amino acid.

It is preferred that $A^1$ and $A^4$ independently from each other designate a residue of an amino acid selected from proline and L-thiazolidine-4-carboxylic acid;

- $A^2$ and $A^3$, independently from each other designate a residue of an amino acid selected from lysine and asparagine; $A^5$ is absent or designates an amino acid selected from serine, threonine, asparagine, and alanine; $A^6$ is absent or designates an amino acid selected from the group consisting of aspartic acid, glutamic acid, and alanine; $A^7$ is absent or designates a residue of an amino acid selected from the group consisting of alanine, phenylalanine, valine, threonine and serine; and $A^8$, $A^9$, and $A^{10}$ independently from each other are absent or designate an amino acid selected from the group consisting of alanine, valine, isoleucine, and proline.

It is especially preferred that the substituents (when present) are selected from the above-identified amino acid residues which have been demonstrated to exist in native OspC. In the most preferred embodiment, the peptide of the invention has the amino acid sequence SEQ ID NO: 1 or a subsequence thereof which includes the 5 C-terminal amino acid residues.

The use of non-naturally occurring amino acid residues in the sequence of a peptide of the invention has as an advantage that the peptide will be relatively resistant to in vivo degradation by peptidases. This effect should render possible the production of stable vaccines incorporating the inventive peptides of the invention, cf. the discussion below of vaccines.

The peptide which is used in the present invention may form part of a larger polypeptide fragment. According to the invention, this polypeptide fragment preferably has a length of at most 60 amino acid residues, but shorter polypeptide fragments are preferred, since these are easier and more economical to synthesize, and since it is preferred that the polypeptide fragment of the invention is a synthetically produced polypeptide fragment.

Hence, in important embodiments of the inventive method, it is preferred that the polypeptide fragment has a length of at most 50 amino acid residues, such as at most 40, 35, 30, 25, and 20 amino acid residues. It is expected that the peptides having a length of between 10 and 20 amino acid residues will prove to be most efficient as diagnostic tools, and therefore especially preferred lengths of the polypeptide fragment used in the inventive method are 18, such as 15, 14, 13, 12 and even 11 amino acid residues. In the most preferred embodiment of the inventive method, the polypeptide fragment is identical to the peptide as defined above, i.e. the polypeptide fragment is defined as the peptide described in detail above.

As discussed herein, the immunological sensitivity in detecting Lyme borreliosis (or more specifically: in detecting antibodies against OspC) is surprisingly high when using a C-terminal fragment of OspC (when compared with the sensitivity of full-length OspC). In the experiments disclosed herein, a sensitivity of 85% of that of full-length OspC has been demonstrated, but OD-titers in an ELISA using the short peptides are significantly higher than those from the rOspC ELISA. It is therefore expected that the immunological sensitivity of an assay which employs the short peptides can be enhanced by optimizing the conditions of the pertinent assay, and therefore it is preferred that the method of the invention exhibits an immunological average sensitivity in detecting randomly selected antisera from patients suffering from early stage Lyme borreliosis which is at least 85% of that achieved by using full-length recombinant OspC in an otherwise corresponding assay. It is however, expected that even higher sensitivities can be achieved (cf. the discussion above relating to sensitivity and cutoff-values) and therefore average immunological sensitivities of at least 90%, such as at least 95%, 98%, 100%, and even at least 105%, such as at least 110%, 120%, 150%, 175%, and 200%, are expected to be possible within the scope of the invention.

In order to enhance the immunorecognition, the immunological agent used in the inventive method can comprise at least two copies of the peptide described above, since more copies of the essential epitope will then be accessible for reaction with immunoglobulins. The inclusion of more than 1 copy of the peptide can be achieved in a number of ways known in the art. For example, the immunological agent may comprise a "backbone" (e.g. a polymer) whereto numerous copies of the inventive peptide (or polypeptide fragment) are coupled N-terminally so as to present a large number of the essential epitope. A similar result can also be achieved by the polypeptide fragment being constituted of at least two consecutive copies of the inventive peptide, or the immunological agent may simply be a conventional carrier substance which can bind the peptide (or polypeptide fragment in a non-specific manner). However, since it has been demonstrated (cf. Example 3) that the free carboxylic acid group in the C-terminal amino acid is essential for the immune diagnostic properties of the peptides of the invention, it is preferable to expose this part of the peptide to the environment wherein the diagnostic assay is performed. Hence, the carrier should normally be one which either binds the polypeptide fragment N-terminally, or at least one which does not impair the immunological properties of the C-terminal amino acid of the peptide of the invention.

In another embodiment of the method of the invention, other OspC derived epitopes (i.e. amino acid stretches of at least 5 amino acids having immunological properties) are included in the sequence of the polypeptide fragment of the invention. This will probably enable further immunological sensitivity.

In a very important embodiment, the inventive method utilises several (at least 2) different immunological agents, wherein the immunological agents differ in the amino acid sequence of the polypeptide fragment, preferably in the amino acid sequence of the peptide. The rationale behind this embodiment is the natural variation in the 10 C-terminal amino acid residues which is described above. It is expected that an assay which takes this natural variability into consideration by incorporating known natural variants of these peptides (or analogues of these known variants) in the immunological agent of the invention will prove more sensitive than the assays which are exemplified herein, since antibodies directed against these phenotypic variants of OspC will be more likely to interact with the immunological agent(s).

It is a preferred embodiment to combine the present diagnostic method with other diagnostic assays for Lyme borreliosis (i.e. assays for previous sensitization with *Borrelia burgdorferi* sensu lato antigens), because, as shown in the examples, the overall sensitivity of such a combined assay is better in the early stages of Lyme borreliosis than one single assay for flagellum antibodies. It is especially preferred that the combination assay comprises an assay for the presence of antibodies against the flagellum of *Borrelia burgdorferi* sensu lato.

It will be understood that the present inventive method can be carried out both in vitro and in vivo. In the following, the in vitro methods will be discussed:

When performed in vitro, the inventive method relies on either 1) the detection of a significant immunological reaction between anti-OspC antibodies and the immunological agent or 2) the detection of a significant immunological reaction between primed T-cells and the immunological agent. In the first case, the immunoassay generally comprises immobilizing immunoglobulins to be detected, adding the immunological agent and thereafter detecting the degree of immunological agent bound to the immunoglobulins, optionally by the immunological agent being labelled or by adding a labelled substance, such as a labelled antibody, which specifically recognizes the immunological agent, immobilizing the immunological agent, adding the immunoglobulins and thereafter detecting the amount of immunoglobulins bound to the immunological agent, optionally by adding a labelled substance, such as a labelled antibody, which specifically recognizes the immunoglobulins, or reacting the immunoglobulins and the immunological agent without any of the reactants being immobilized and subsequently detecting the amount of complexes of immunological agent and immunoglobulins, optionally by the immunological agent being labelled or by adding a labelled substance, such as a labelled antibody, which specifically recognizes the immunological agent.

Immobilization of the immunological agent can be either covalent or non-covalent and the non-covalent immobilization can be non-specific (e.g. non-specific binding to a polystyrene surface in e.g. a microtiter well). Specific or semi-specific binding to a solid or semi-solid carrier, support or surface, can be achieved by the immunological agent, in addition to the polypeptide fragment, further comprising a moiety which enables covalent or non-covalent binding of the polypeptide fragment to a solid or semi-solid carrier, support or surface. Specifically, non-covalent binding to the carrier, support or surface can be enabled by this moiety having affinity to a component attached to the carrier, support or surface. In this case, the moiety may be a biotin or biotinyl group or an analogue thereof bound to an amino acid group of the polypeptide fragment, such as 6-aminohexanoic acid, and the component is then avidin, streptavidin or an analogue thereof. An alternative is a situation where the moiety has the amino acid sequence His-His-His-His-His-His, and where the carrier comprises a Nitrilotriacetic Acid derivative (NTA) charged with $Ni^{++}$ ions.

The protocols for immunoassays using antigens for detection of specific antibodies are well known in art. According to the invention the peptide, polypeptide fragment or immunological agent may be employed in sandwich assays for detecting antibodies in Lyme borreliosis patients or in the known modifications and variations of sandwich assay protocols. Alternatively, the antibodies and antigen binding fragments thereof may be employed in various competitive assay formats as are known in the art. The basics of these assay protocols are reviewed in Current Protocols in Immunology (1995). When used as a diagnostic for Lyme borreliosis, it is preferred to use a solid phase assay.

Hence, it is preferred that the method of the invention is one, wherein the immunological agent is immobilized to the solid or semi-solid surface or carrier by means of covalent or non-covalent binding, either prior to or after the addition of the immunoglobulins. In this connection, it should be remembered that the immobilization should leave free the carboxylic acid group of the C-terminal amino acid in the peptide of the invention constituting part of the immunological agent, cf. the above discussion.

Devices for performing specific binding assays, especially immunoassays, are known and can be readily adapted for use with the present peptides for detecting anti-borrelia antibodies. Solid phase assays, in general, are easier to perform than heterogeneous assay methods such as precipitation assays because separation of reagents is faster and simpler. Solid-phase assay devices include microtiter plates, flow-through assay devices, dipsticks and immunocapillary or immunochromatographic immunoassay devices.

Thus, the solid or semi-solid surface or carrier can, according to the invention be the floor or wall in a microtiter well; a filter surface; a hollow fibre; a beaded chromatographic medium selected from an agarose or polyacrylamide gel; a magnetic bead; a fibrous cellulose matrix; an HPLC matrix; an FPLC matrix; a substance having molecules of such a size that the molecules with the immunological agent bound thereto, when dissolved or dispersed in a liquid phase, can be retained by means of a filter; a substance capable of forming micelles or participating in the formation of micelles allowing a liquid phase to be changed or exchanged without entraining the micelles; a water-soluble polymer; or any other suitable carrier, support or surface.

In some embodiments of the invention, the immunological agent may be provided with a suitable label which enables detection. It is also possible that detection is effected by using a substance having affinity for the immunological agent or for the pertinent immunoglobulins, and such a substance (normally an antibody) can also be provided with a suitable label. Such a label can e.g be a radioactive, an enzymatic, a fluorescent, and any other detectable label such as an avidin/biotin system.

More specifically, a wide variety of appropriate indicator means are known in the art, including radioactive, enzymatic or other ligands, such as avidin/biotin, which are capable of giving a detectable signal. In preferred diagnostic embodiments, one will likely desire to employ an enzyme tag such as alkaline phosphatase or peroxidase, instead of radioactive or other environmentally undesirable reagents. In the case of enzyme tags, calorimetric indicator substrates are known which are employed to provide a means visible to the human eye or spectrophotometrically, to identify specific hybridization with pathogen nucleic acid-containing samples. Luminescent substrates, which give off light upon enzymatic degradation, could also be employed and may provide increased sensitivity.

It is preferred that the detection of the degree of immunological reactivity in the method of the invention is effected by means of an immunoassay selected from the group consisting of a direct or indirect EIA such as an ELISA, an immunoblot technique such as a Western blot (cf. the experiment described in Example 4), an RIA, and any other non-enzyme linked antibody binding assay or procedure such as a fluorescence, agglutination or precipitation reaction, and nephelometry.

Since infection with *Borrelia burgdorferi* sensu lato does not seem to give rise to any significant anti-OspC IgG response in humans it is preferred that the immunoglobulins which are detected according to the invention are of IgM, IgE, IgD or of IgA type. IgM antibodies are especially preferred, since these are indicative of ongoing or very recent infection. This will therefore supplement e.g. IgG sensitive assays for the flagellum, since a positive response in such a test can be indicative of both ongoing, recent and prior infection.

Although the present examples have only demonstrated the efficacy of the C-terminal peptides in diagnosing a humoral immune response, it is expected that also a cell-mediated immune response can be detected, since the essential epitope most likely is linear and since T-cell epitopes always are linear. Hence, it is expected that the essential epitope in the C-terminus will also function as a T-cell epitope.

It is therefore expected that it will also be possible to determine the immunological reactivity between primed T-cells and the immunological agent of the invention. In vitro this can be done by incubating T-cells isolated from the subject with the immunological agent and measuring the immunoreactivity, e.g. by measuring subsequent T-cell proliferation or by measuring release of cytokines from the T-cells, such as IFN-γ; these methods are well-known in the art, but are e.g. disclosed in EP-A-706571.

When the method of the invention is carried out in vivo, it is desirable to do this in the form of a skin test, i.e. by intradermally injecting, in the subject, the immunological agent or the polypeptide fragment described above, a positive skin response at the location of injection being indicative of the person having and/or having had Lyme borreliosis, and a negative skin response at the location of injection being indicative of the person not having and/or having had Lyme borreliosis. Thus, the in vivo version of the method of the invention relies on the detection of a T-cell response in the subject.

Another part of the invention relates to the immunological agent defined above, i.e. all considerations concerning the immunological agent used in the method of the invention also applies *mutatis mutandis* to the immunological agent of the invention. That is, all discussions pertaining to the polypeptide fragment and the peptide comprised in the immunological agent as well as all discussions relating to the nature of the immunological agent with respect to labels and coupling to carriers etc. are relevant also for the immunological agent of the invention.

Likewise, another part of the invention pertains to the polypeptide fragment discussed above, and likewise, all considerations concerning the polypeptide fragment used in the inventive method also applies *mutatis mutandis* to the polypeptide fragment of the invention.

Consequently, a fourth part of the invention is a peptide as defined in relation to the inventive method and also with respect to this aspect of the invention, all the above considerations, definitions etc. concerning the peptide used in the inventive method applies *mutatis mutandis* to the inventive peptide.

In line with the above, the invention also relates to the uses of the immunological agent of the invention, the polypeptide fragment of the invention and the peptide of the invention for in vivo diagnosis as well as to the uses thereof for the preparation of an diagnostic composition/agent for the specific in vivo diagnosis of previous sensitization in a subject with OspC from *Borrelia burgdorferi* sensu lato.

Also methods for preparation of the immunological agent of the invention, the polypeptide fragment of the invention and the peptide of the invention are embraced by the following invention. The peptide and polypeptide fragment can both be produced by either chemical synthesis (by solid or liquid phase synthesis) or by recombinant DNA technology.

In principle, the peptide and/or polypeptide fragment may be synthesized using any method for solid-phase or liquid-phase peptide synthesis known in the art, for example the solid-phase method of Merrifield (Merrifield (1969)) or the modified solid-phase methods of Sheppard and Atherton (WO 86/03494) which are now both automated. Also the well-known methods of liquid-phase synthesis are useful, but solid-phase synthesis is preferred.

When producing the peptide or polypeptide fragment by means of recombinant technology, the process comprises inserting a nucleic acid fragment encoding the polypeptide fragment or peptide (optionally coupled to a nucleic acid fragment encoding a suitable fusion partner) into a vector which is able to replicate in a host cell, introducing the resulting recombinant vector into the host cell, culturing the host cell in an appropriate culture medium under appropriate conditions for expressing the polypeptide fragment or peptide (and the optional fusion partner), and recovering the polypeptide fragment or peptide (together with the optional fusion partner) from the host cell or culture medium, optionally cleaving the optional fusion partner from the polypeptide fragment or peptide, and isolating and/or purifying the thus produced polypeptide fragment or peptide.

When producing the immunological agent, the methods of producing the polypeptide fragment or the peptide are combined with a step wherein the polypeptide fragment or peptide is coupled to or admixed with the moiety or label discussed above.

All the production methods are combined with a step where the product is at least partially purified or isolated.

The selected device and reagents for performing the method of the invention may be packaged in the form of a kit for convenience. For example, such a kit may include an appropriate assay device, coating reagents, reagents for development of the assay such as buffers and reagents for detection of the chosen label. Such a kit is of course helpful in reducing the risk of developing the second and third stages of Lyme borreliosis, since treatment of such infection can be instituted once it is diagnosed. Therefore, the invention relates to a kit which comprises, in one package, an immunological agent according to the invention, together with means enabling detection of specific binding between the immunological agent and immunoglobulins specifically reactive with OspC protein.

Another aspect of the invention is an immunological composition for raising an immune response in an animal, including a human being, the immunological composition comprising an immunological agent according to the invention (or a polypeptide fragment according to the invention or a peptide according to the invention) in combination with a physiologically acceptable carrier and/or vehicle and optionally also in combination with an adjuvant substance. It is preferred that the immunological composition is in the form of a vaccine (i.e. that it provides a protective effect in animals and/or humans against infections with *Borrelia burgdorferi* sensu lato), but the immunological composition may also be used for immunization with a view to antibody production in suitable animals. Such antibodies will be important diagnostic means also.

As briefly discussed in the examples, no significant level of IgG reactive with OspC can be found in sera from Lyme borreliosis patients. It therefore seems that patients suffering from Lyme borreliosis do not (or do only occasionally) develop an IgG response to OspC. On the other hand, because of the appearance of IgM in the early stages of the disease, it is evident that OspC is in fact immunogenic. The question therefore arises whether it would be possible to mount an immune response involving IgG by use of the peptides of the invention as an immunogenic agent. If the peptide is administered in a suitable formulation (e.g. in combination with a suitable adjuvant), it should be possible to provoke the production of IgG against OspC, and thereby increase the resistance against infections caused by *Borrelia burgdorferi* sensu lato. Even if a protective immune response cannot be mounted, the peptides of the invention will also be useful in the production of specific antibodies against OspC.

Hence, even though the human immune system in the majority of cases only raises an IgM response against OspC, it is regarded as possible to raise a protective IgG response also in humans if a suitable combination of adjuvant and antigen is formulated and used as a immunizing agent.

The invention therefore also relates to a method for immunizing an animal (including a human being) against OspC protein derived from *Borrelia burgdorferi* sensu lato, the method comprising administering an immunogenically effective amount of an immunological composition defined above.

In line with this, the invention also relates to the uses of the immunological agent of the invention, the polypeptide fragment of the invention and the peptide of the invention as a pharmaceutical (a vaccine) as well as to the uses thereof for the preparation of a vaccine against infections with *Borrelia burgdorferi* sensu lato.

An especially interesting embodiment of the present part of the invention relates to a vaccine, wherein at least one of the naturally occurring amino acids in a peptide of the invention has been replaced by a non-naturally occurring one, since such a peptide will be much more resistant to degradation by peptidases (cf. the data on diagnostic efficacy of one such variant in Example 3, suggesting that also some of such variants will be immunologically active). Hence, a prolonged biological half-life of a vaccinating agent can be achieved, an effect which should lead to an improved efficacy of the vaccine due to a longer effective time of immunization.

Preparation of vaccines which contain peptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables either as liquid solutions or suspensions; solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like, and combinations thereof In addition, if desired, the vaccine may contain minor amounts of auxiliary substances such as wetting or emulsifying agents, pH buffering agents, or adjuvants which enhance the effectiveness of the vaccines.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides; such suppositories may be formed from mixtures containing the active ingredient in the range of 0.5% to 10%, preferably 1–2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10–95% of active ingredient, preferably 25–70%.

The peptide sequences may be formulated into the vaccine as neutral or salt forms. Pharmaceutically acceptable salts include acid addition salts (formed with the free amino groups of the peptide) and which are formed with inorganic acids such as, for example, hydrochloric or phosphoric acids, or such organic acids as acetic oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, including, e.g., the capacity of the individual's immune system to mount an immune response, and the degree of protection desired. Suitable dosage ranges are of the order of several hundred micrograms active ingredient per vaccination with a preferred range from about 0.1 $\mu$g to 1000 $\mu$g, such as in the range from about 1 $\mu$g to 300 $\mu$g, and especially in the range from about 10 $\mu$g to 50 $\mu$g. Suitable regimes for initial administration and booster shots are also variable but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the age of the person to be vaccinated and, to a lesser degree, the size of the person to be vaccinated.

Some of the polypeptides of the vaccine are expected to be sufficiently immunogenic in a vaccine, but for some of the others the immune response may be enhanced if the vaccine further comprises an adjuvant substance.

Various methods of achieving adjuvant effect for the vaccine include use of agents such as aluminum hydroxide or phosphate (alum), commonly used as 0.05 to 0.1 percent solution in phosphate buffered saline, admixture with synthetic polymers of sugars (Carbopol) used as 0.25 percent solution, aggregation of the protein in the vaccine by heat treatment with temperatures ranging between 70° C. to 101° C. for 30 second to 2 minute periods respectively. Aggregation by reactivating with pepsin treated (Fab) antibodies to albumin, mixture with bacterial cells such as *C. parvum* or endotoxins or lipopolysaccharide components of gram-negative bacteria, emulsion in physiologically acceptable oil vehicles such as mannide mono-oleate (Aracel A) or emulsion with 20 percent solution of a perfluorocarbon (Fluosol-DA) used as a block substitute may also be employed. Other interesting candidates for adjuvants are DDA (dimethyldioctadecylammonium bromide), but also Freund's complete and incomplete adjuvants as well as QuilA and RIBI are interesting possibilities.

Other possibilities involve the use of immunomodulating substances such as lymphokines (e.g. IFN-$\gamma$, IL-2 and IL-12) or synthetic IFN-$\gamma$ inducers such as poly I:C in combination with the above-mentioned adjuvants.

In many instances, it will be necessary to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1–5 years, usually three years, will be desirable to maintain the desired levels of protective immunity. The course of the immunization may be followed by in vitro assays. The assays may be performed using conventional labels, such as radionuclides, enzymes, fluorescers, and the like. These techniques are well known and may be found in a wide variety of patents, such as U.S. Pat. Nos. 3,791,932; 4,174,384 and 3,949,064, as illustrative of these types of assays.

It is also possible to produce a living vaccine by introducing, into a non-pathogenic microorganism, at least one nucleic acid fragment encoding a polypeptide fragment or peptide of the invention, and effecting expression of the polypeptide fragment or the peptide on the surface of the microorganism (e.g. in the form of a fusion peptide including a membrane anchoring part or in the form of a sligthly modified peptide or polypeptide fragment carrying a lipidation signal which allows anchoring in the membrane). The skilled person will know how to adapt relevant expression systems for this purpose.

Another part of the invention is based on the fact that recent research have revealed that a DNA fragment cloned in a vector which is non-replicative in eukaryotic cells may be introduced into an animal (including a human being) by e.g. intramuscular injection or percutaneous administration (the so-called "gene gun" approach). The DNA is taken up by e.g. muscle cells and the gene of interest is expressed by a promoter which is functioning in eukaryotes, e.g. a viral promoter, and the gene product thereafter stimulates the immune system. These newly discovered methods are reviewed in Ulmer et al., 1993, which hereby is included by reference.

Thus, a nucleic acid fragment encoding a polypeptide or peptide of the invention may be used for effecting in vivo expression of antigens, i.e. the nucleic acid fragments may be used in so-called DNA vaccines. Hence, the invention also relates to a vaccine comprising a nucleic acid fragment encoding a polypeptide fragment or a peptide of the invention, the vaccine effecting in vivo expression of antigen by an animal, including a human being, to whom the vaccine has been administered, the amount of expressed antigen being effective to confer substantially increased resistance to infections with *Borrelia burgdorferi* sensu lato in an animal, including a human being.

The efficacy of such a "DNA vaccine" can possibly be enhanced by administering the gene encoding the expression product together with a DNA fragment encoding a polypeptide which has the capability of modulating an immune response. For instance, a gene encoding lymphokine precursors or lymphokines (e.g. IFN-γ, IL-2, or IL-12) could be administered together with the gene encoding the immunogenic polypeptide fragment or peptide, either by administering two separate DNA fragments or by administering both DNA fragments included in the same vector. It is also a possibility to administer DNA fragments comprising a multitude of nucleotide sequences which each encode relevant epitopes of the polypeptide fragments and peptides disclosed herein so as to effect a continuous sensitization of the immune system with a broad spectrum of these epitopes (e.g. from different serotypes of OspC which are non-identical in their C-terminal epitope).

The following experimental non-limiting examples are intended to illustrate certain features and embodiments of the invention.

MATERIALS AND METHODS USED IN THE EXAMPLES

Synthesis of Immunological Agent Containing C-terminally Derived Peptides.

The "model" antigenic peptide has the amino acid sequence: $NH_2$-Pro-Val-Val-Ala-Glu-Ser-Pro-Lys-Lys-Pro-COOH (SEQ ID NO: 1). This peptide constituted the starting point of the synthesis of a series of variants, cf. below.

When used directly in an ELISA, the "model" peptide and certain of the variants were coupled to a 6-amino hexanoic acid residue at the N-terminus. This residue serves as a spacer linkage between the carrier and the peptide. While not wishing to be limited to any particular method by which the invention operates, applicants believe that by providing such a spacer linkage, the negative effects of the binding to the ELISA plates on the conformation of the peptide may be reduced, thus allowing the peptide to assume a conformation more characteristic of a naturally occurring epitope of the OspC protein.

In the present examples, synthetic peptides were synthesized by automated solid phase synthesis, followed by purification by HPLC and sequence verification by mass spectroscopy. In details, the preparation of the peptides was performed as follows:

Solid-phase peptide synthesis was performed with the fluor-enylmethoxycarbonyl (Fmoc) strategy by use of multiple-column peptide synthesis as described previously in Holm (1989) and Meldal (1993). All peptides were synthesized with Fmoc amino acids (MilliGen and Calbiochem-Novabiochem) using TBTU (O-(1H-benzotriazol-1-yl)-1,1,3,3-tetramethyluronium tetrafluoroborate) and HOBt (N-hydroxy-benzotriazole) as coupling agents. Asn (MilliGen) was used with trityl, Lys (MilliGen) with tBoc (tert. butyloxycarbonyl), Glu and Ser (MilliGen) with tBu (tert. butyl), and Arg (MilliGen) with Pmc (2,2,5,7,8-pentamethylchroman-6-sulfonyl) side-chain protection. The following non-protein aminoacids were coupled in the same way: N-$_\alpha$-Fmoc-N-$_\beta$-Boc-L-diaminopropionic acid, Fmoc-O-t-Butyl-L-hydroxyproline, Fmoc-L-indoline-2-carboxylic acid, N-$_\alpha$-Fmoc-N-$_\alpha$-Boc-diaminoacetic acid, N-$_\alpha$-Fmoc-N-$_\gamma$-Boc-L-diaminobutyric acid, Fmoc-1,2,3,4-L-tetrahydroisoquinoline-3-carboxylic acid, Fmoc-L-thiazolidine-4-carboxylic acid, (Neosystems Laboratoire, Strassbourg, France), Fmoc-Homopro-OH (Bachem Feinchemika-lien AG, Germany), Fmoc-L-Orn (Boc)-OH (Novabiochem), Fmoc-D-Arg(Pmc)-OH, Fmoc-D-Lys(Boc)-OH, and Fmoc-D-Pro-OH (Nova-biochem)

0.4 M solutions (DMF (dimethylformamide) of the amino acids (3 times excess) containing eqv. amounts of TBTU and HOBt and 1.5 eqv of DIEA (diisopropylethylamine) (Aldrich) were used for the couplings. An acid-labile H-Pro-2-ClTrt resin (Novabiochem; s=0.8 mmol/g)) was used for preparation of C-terminal proline containing peptide carboxylates. For peptide carboxamides a PepSyn K resin (Novabiochem) fitted with an AM-linker (Novabiochem) was used (s Å 0.1 mmol/g). DMF was purified prior to use on a cation exchanger column packed with Lewatit S 100 MB/H (Bayer AG Leverkusen, Germany).

Biotinylated 6-amino-hexanoic-peptides were prepared as after assembly of the peptide chain and Fmoc-deprotection using TBTU and HOBt as coupling reagents.

The assembled peptides were cleaved from the resin with TFA (trifluoroacetic acid)-$H_2O$ -thioanisole (90:5:5, vol/vol/vol) at room temperature for 2 h and then washed with TFA-$H_2O$ (95:5, vol/vol). The combined TFA washes were concentrated in vacuo, and the peptide was precipitated and washed with ether, dried and lyophilized from water except for the 4–6 mer peptides which were lyophilized from water after concentration of the combined TFA washes and then washed with ether. HPLC (high performance liquid chromatography) was performed on a Waters Millenium HPLC system with a C18 reversed-phase column (Waters Rad-Pak Delta-Pak C18, 15 mm, 100 Å, 8 mm×100 mm; flow rate 1.5 ml/min, for analytical separations), buffer A (0.1% TFA), and buffer B (0.1% TFA and 10% water in acetonitrile), and amino acid analyses were performed with a Waters PICOTAG system. All compounds were better than ≈90% pure according to the analysis. The identity of all peptides was verified by MALDI TOF (matrix assisted laser desorption ionization time of flight) mass spectroscopy with a Fisons TofSpec E instrument. For ELISA the concentration of the peptide samples were determined by amino acid analysis performed with the PICOTAG system (Waters).

Production of $rOspC_{fl}$ and $rOspC_t$

The $rOspC_{fl}$ proteins used were derived from strain DK7 of *Borrelia burgdorferi* sensu stricto (having the amino acid sequence SEQ ID NO: 5 and encoded by SEQ ID NO: 4), strain DK6 of *Borrelia garinii* (having the amino acid sequence SEQ ID NO: 3 and encoded by SEQ ID NO: 2), and strain DK26 of *Borrelia afzelii* (having the amino acid sequence SEQ ID NO: 7 and encoded by SEQ ID NO: 6), respectively. The $rOspC_{fl}$ proteins were produced in the following way:

The ospC genes encoding the above-indicated $OspC_{fl}$ sequences were amplified from genomic DNA by using standard PCR conditions and three primer sets specific for either *B. garinii* DK6: BF22 (5'-ATA GAT ATC AAT AAT TCA GGT GGG GAT TC-3' [SEQ ID NO: 8]) and BF65 (5'-TTT GAT ATC TCA AGG TTT TTT TGG ACT TTC TGC-3' [SEQ ID NO: 9]); *B. burgdorferi* sensu stricto DK7: BF26 (5'-ATA GAT ATC AAT AAT TCA GGA AAA GAT GGG AAT AC-3' [SEQ ID NO: 10]) and BF65; or *B. afzelii* DK26: BF24 (5'-ATA GAT ATC AAT AAT TCA GGG AAA GGT GGG G-3' [SEQ ID NO: 11]) and BF65. All primers contain non-homologous sequences to facilitate the subsequent cloning of the PCR products. The genes were cloned into pMST24 generating plasmids pBF144, pBF147, and pBF145.

pMST24 is an expression plasmid containing unique restriction sites allowing the construction of in frame fusions with an artificial leader peptide composed of a stretch of six His residues followed by a bovine factor $X_a$ cleavage site. The mRNA for the corresponding peptide is translated from a plasmid-encoded translational start site and controlled by a tac promoter. The plasmid also encodes the lac repressor to ensure tight control of gene expression.

Protein production was induced by adding 2 mM IPTG to a late log culture of XL1blue harbouring either pBF144, pBF147, or pBF145.

Six consecutive histidine residues (6×His) will selectively bind $Ni^{2+}$, allowing purification of the fusion proteins by metal chelate affinity chromatography. Fusion proteins were purified on a $Ni^{2+}$-IDA (Iminodiacetic acid-epoxy activated Sepharose 6B fast flow (Sigma Chemical Co., St. Louis, Mo.)) column as described in detail in the QIAexpressionist, protocol 5, page 42–43. To the harvested cells from the culture was added enzyme inhibitors (Peptstatin (1 μg/ml), PMSF (100 μg/ml), Aprotinin (1 μg/ml), and TLCK (50 μg/ml)) before sonication, as well as all buffers used in the purification.

The $OspC_t$ were obtained by an identical method, but the purified product lacked the seven C-terminal amino acids. The primers used were as follows: For *B. garinii* DK6: BF22 and BF23 (5'-TTT GAT ATC TCA CAC AAC AGG ATT TGT AAG CTC TTT AAC-3' [SEQ ID NO: 12]); for *B. burgdorferi* sensu stricto DK7: BF26 and BF27 (TTT GAT ATC TCA CAC AAC AGA CTG TAA GCT CTT AAC TGA AT-3' [SEQ ID NO: 13]); and for *B. afzelii* DK26: BF24 and BF25 (5-'TTT GAT ATC TCA TAC AAC AGG ACT TGT AAG TTC TTT AAC TGA-3' [SEQ ID NO: 14]).

Indirect ELISA for IgM Antibodies to Full-length and Truncated Recombinant OspC (rOspC ELISA)

Flat-bottom microdilution plates (Maxisorb; Nunc, Roskilde, Denmark) were coated with 100 μl of rOspC diluted in 0.05 M bicarbonate pH 9.6 for 1 hour at 20° C. on a rocker platform and thereafter overnight at 4° C. The optimum coating concentration was defined as the antigen dilution resulting in the highest ratio of the optical density (OD) between a positive and a negative control serum (P/N ratio). The plates were washed four times à one minute with PBS containing 0.5 M NaCL, and 0.1% (vol/vol) Tween 20 (pH 7.2) and unspecific protein binding was blocked with 100 μl 3% (wt/vol) milk powder in PBS for 1 hour. The plates were washed four times à one minute with PBS containing 0.5 M NaCL, and 0.1% (vol/vol) Tween 20 (pH 7.2). 100 μl of serum diluted 1:200 in PBS containing 0.1% (vol/vol) Tween 20, 0.02% $NaN_3$ and 1% (wt/vol) milk powder was added to the wells and incubated for 2 h at 20° C. The plates were washed four times à one minute with PBS containing 0.5 M NaCL, and 0.1% (vol/vol) Tween 20 (pH 7.2) and 100 μl peroxidase conjugated rabbit anti-human immunoglobulin M (IgM) (Dakopats, Copenhagen, Denmark, code P-215) diluted 1:1000 in PBS pH 7.4 with 0.05% (vol/vol) Tween 20 and 1% (wt/vol) milk powder. After the incubation for 1 h at 20° C. the plates were washed four times à one minute with PBS containing 0.5 M NaCL, and 0.1% (vol/vol) Tween 20 (pH 7.2) and 200 μl of the substrate o-phenylenediamine (0.41 mg/ml; Sigma) in citrate buffer (pH 5) with 0.04% (vol/vol) $H_2O_2$) was added to each well. After 15 minutes protected from light, the enzymatic reaction was stopped by the addition of 50 μl of 3M $H_2SO_4$. The optical density (OD) at 492 nm was read spectrophotometrically (Immuno Reader, Easy reader EAR 400 AC—SLT Labinstruments, AUSTRIA). Samples were tested in duplicate and retested, if the two OD values differed more than 10% from the mean. To eliminate plate-to-plate and day-to-day variations, a reference serum pool based on seven western blot positive sera were included on every plate for construction of a standard dilution curve with a two fold dilution ranging from 1:200 to 1:6400. The OD value of every sample was adjusted to this standard curve. Positive and negative control sera were included on every plate. The positive control sera were diluted 1:200, 1:400 and 1:800 on every plate to check for parallelism between the standard reference curve and the dilution curve of the positive control sera.

The total assay precision of the rOspC ELISA was determined by testing the positive control sera in 20 independent assays. Examination of a positive control serum diluted out three times showed mean OD values for the dilution 1:200 of 1.829, standard deviation (SD) 0.148 and a variation coefficient (CV) of 10%; mean OD values for dilution 1:400 of 0.965 with SD 0.101 and CV 15%; mean OD values for dilution 1:800 of 0.502 with SD 0.053, and CV 11%.

The diagnostic cutoff OD was adjusted to be 98% specific for an IgM assay on the basis of serum samples from 100 healthy danish blood donors, and was 0.230 for the IgM assay.

Indirect Streptavidin ELISA for IgM Antibodies against Carboxy-terminal OspC Deca-peptide (Peptide ELISA)

Flat-bottom microdilution plates (Maxisorb; Nunc, Roskilde, Denmark) were coated with 100 μl of streptavidin (ZYMED, *S. Avidinii*) 2.5 μg/ml in citrate buffer (pH 5) and incubated overnight at 4° C. The plates were washed four times a one minute with phosphate buffered saline (PBS) containing 0.5 M NaCl and 0.1% (vol/vol) Tween 20 (pH 7.2), 100 μl of the biotinylated synthetic peptide

```
                                        (SEQ ID NO: 40)
6-aminohexanoic acid-Pro-Val-Val-Ala-Glu-Ser-Pro-
Lys-Lys-Pro
```

(prodiluted in PBS containing 0.37 M NaCl, 0.5% (vol/vol) Tween 20, and 1% (wt/vol) milk powder (pH 7.0)) was added to the wells and the plates were incubated overnight at 4° C. The plates were washed four times a one minute with PBS containing 0.5 M NaCl and 0.1% (vol/vol) Tween 20 (pH 7.2), and 100 μl of test serum diluted 1:200 in PBS containing 0.7 M NaCl, 0.1% (vol/vol) Tween 20, and 1% (wt/vol) milkpowder (pH 7, 2) was added to the wells and incubated for 2 hours at 20° C. on a rocker platform. The plates were washed four times à one minute with PBS containing 0.5 M NaCl and 0.1% (vol/vol) Tween 20 (pH 7.2), and 100 μl of peroxidase conjugated rabbit anti-human IgM (code P215; Dako-patts, Copenhagen, Denmark) diluted 1:1000 in PBS containing 0.5% Tween 20 and 1% milkpowder (pH 7.4) was added to the wells and incubated for 1 h at 20° C. The plates were washed four times à one minute with PBS containing 0.5 M NaCl and 0.1% (vol/vol) Tween 20 (pH 7.2), and 200 μl of the substrate o-phenylenediamine (0.33 mg/ml; Kem-En-Tec, Denmark, tablets of 10 mg) in citrate buffer (pH 5) with 0.04% (vol/vol) $H_2O_2$ was added to each well. After 15 minutes protected from light, the enzymatic reaction was stopped by the addition of 50 μl of 3 M $H_2SO_4$. The optical density (OD) at 492 nm was read spectrophotometrically on an Immuno Reader, Easy reader EAR 400 AC, SLT Labinstruments, AUSTRIA. Samples were tested in duplicate and retested if the two OD values differed more than 10% from the mean. To eliminate plate-to-plate and day-to-day variations, a reference serum pool based on seven western blot positive sera were included on every plate for construction of a standard dilution curve with a two fold dilution ranging from 1:200 to 1:6400. The OD value of every sample was adjusted to this standard curve. Positive and negative control sera were included on every plate. The positive control sera were diluted 1:200, 1:400 and 1:800 on every plate to check for parallelism between the standard reference curve and the dilution curve of the positive control sera.

The diagnostic cutoff OD was adjusted to be 98% specific for IgM on the basis of serum samples from healthy danish blood donors, and was 0.450 for the IgM assay.

Example 1

Immunological Reactivity of Full-length and Truncated rOspC ($rOspC_{fl}$ and $rOspC_t$) with Antisera from Patients Suffering from *Lyme Borreliosis*

In a preliminary setup, $rOspC_t$ was used in the above-described rOspC ELISA. Sera from 47 patients with EM, 50 with NB, 30 with ACA and 29 with syphilis were tested against $rOspC_t$.

Serum Specimens from Patients

Panel 1 consisted of sera from 117 patients with clinical symptoms of definite, active, and untreated LB:

(i) Sera from 47 Patients with Erythema Migrans (EM).

The diagnosis was culture verified by skin biopsy in 22 patients, and in the remaining 25 cases the diagnosis was based on clinical evidence without previous serological testing. These sera were collected from 1989 to 1992. The median disease duration was 3 weeks and ranged from less than 1 week to one year.

(ii) Sera from 50 Consecutive Patients with Neuroborreliosis (NB) Collected in 1991.

The diagnosis was based on clinical evidence; all but two patients had lymphocytic pleocytosis in CSF; in one patient CSF cytology was not examined, and in the other CSF cytology was referred after antibiotic treatment; both patients had a definite history of clinical neuroborreliosis and positive intrathecal antibody synthesis. All patients had *B. burgdorferi* specific intrathecal antibody synthesis. The median disease duration was 3 weeks and ranged from 1 week to 1½ year after onset of neurological symptoms.

(iii) Sera from 20 Patients with Acrodermatitis Chronica Atrophicans (ACA) Collected from 1987 to 1990.

The clinical diagnosis was in every patient made by a dermatologist. The disease duration ranged from 8 months to 10 years, median 4 years.

Control Serum Specimens (i) Sera from 29 Patients with Early Syphilis having Very High IgM and/or IgG Antibody Levels (OD>1.5) in the Reiter Treponeme Flagellum ELISA.

All sera were positive in WR, RPR and the FTA-absorption test.

(ii) 100 Randomly Collected Sera from Danish Blood Donors.

All sera were stored at −20° C.

Results

In Table 1 are listed the results from the rOspC ELISA performed on serum panel 1 using $rOspC_t$. The results are from *B. garinii* $rOspC_t$, but similar results were found for the truncates of the other two Borrelia strains, in fact no positives were found when using *B. afzelii* derived $rOspC_t$.

TABLE 1

| Patient sera | Positive $rOspC_T$ ELISA results |
|---|---|
| EM (n = 47) | n = 1 (2.12%) |
| NB (n = 50) | n = 3 (6.00%) |
| EM and NB (n = 97) | n = 4 (4.12%) |
| ACA (N = 30) | n = 0 (0.00%) |
| Syphilis (n = 29) | n = 5 (17.24%) |

As is evident, the immunological reactivity of $rOspC_t$ is relatively low and consequently it was concluded that the 7 C-terminal amino acid residues of OspC may be important in the immunological recognition by the human immune system of OspC. Therefore, the immunological reactivity of the C-terminus of OspC as well as of full-length rOspC ($rOspC_{fl}$) was subjected to further investigations, cf the next example.

Example 2

The Diagnostic Performances of a Decapeptide ELISA and an rOspC ($rOspC_{fl}$) ELISA Compared with the Diagnostic Performance of a Commercially Available Flagellum Assay.

The capability of an immunological agent according to the present invention to react with sera from patients in various stages of Lyme borreliosis was evaluated against that of recombinant OspC derived from *B. garinii* and against conventional flagellum ELISAs (performed as described in Hansen K. et al. (1991) and Hansen K. et al. (1988)). These flagellum assays (testing for IgM and IgG antibodies to native *B. burgdorferi* flagellum) are commercially available, a $\mu$-capture ELISA (DAKO, Denmark code K006), and an indirect IgG ELISA (DAKO, Denmark code K416). Both assays use flagella purified from strain DK1 belonging to the genospecies of *B. afzelii*. The ELISAs were performed according to the instructions of the manufacturer, and the results were expressed as optical density (OD) values. In both assays the diagnostic cut-off level was adjusted to a specificity of 98% based on the examination of 100 blood donors.

Although only results from immunoassays using $rOspC_{fl}$ from *B. garinii* are reported here, an almost identical picture could be seen when using $rOspC_{fl}$ from *B. burgdorferi* sensu stricto and *B. afzelii*.

Serum Specimens from Patients

A total of 210 serum specimens from patients with active untreated Lyme borreliosis were tested in the ELISAs. They were divided into three groups according to clinical manifestations of their disease.

(i) Sera from 60 Swedish Patients and 20 Danish Patients with Erythema Migrans (EM).

The diagnoses of 60 Swedish patients with EM were based on clinical evidence and made by Eva Åsbrink (Department of Dermatology, Södersjukhuset, Stockholm, Sweden), and the diagnosis of 20 Danish patients with EM were verified in culture upon skin biopsy. The sera were collected in the period 1984–1992 from patients of between 6 and 83 years of age (median age, 53 years). The disease duration ranged from half a week to 26 weeks (median duration, 4 weeks).

(ii) Sera from 101 Danish Patients with Neuroborreliosis (NB).

One hundred Danish patients with NB were all hospitalized in 1994 (58 males and 42 females of between 4 and 80 years of age; median age, 49). The diagnosis was based on clinical evidence, especially the typical painful sensory radiculitis and lymphocytic pleocytosis in the cerebrospinal fluid (CSF). In many cases, the specificity of the clinical diagnosis was further strengthened by prior observation of a tick bite (31 patients), and prior erythema migrans (42 patients). All had lymphocytic pleocytosis in CSF, with counts of $3\times10^6$ to $1200\times10^6$ cells per liter (median cell count, $123\times10^6$ cells per liter). All patients had intrathecal *B. burgdorferi* specific antibody synthesis. The disease duration, defined as the time after onset of neurological symptoms until a blood sample was taken, ranged from 1 week to 26 weeks (median duration, 3 weeks).

(iii) Sera from 30 Swedish Patients with ACA.

Sera from 30 Swedish patients with acrodermatitis atrophicans (ACA) between 36 and 89 years of age, (median age, 61). The diagnosis was in every case made by a dermatologist on the basis of the typical clinical appearance of ACA and a high IgG titer to *B. burgdorferi* in serum. The disease duration ranged from 1 to 5 years, (median duration, 2 years).

Control Serum Specimens.

Sera from 150 healthy controls were used for determination of the 98%-specific cut-off level in ELISAs. Additionally, sera from 30 patients with early syphilis having very high IgM and/or IgG antibody levels (OD<1.5) in the Reiter treponeme flagellum ELISA were tested. All sera showed a positive Wassermann reaction, a positive rapid plasma reagin test, and a reactivity ≧3+ in the fluorescent treponemal antibody absorption test.

Results

Comparing the Peptide ELISA with the $rOspC_{fl}$ ELISA.

The following table (Table 2) shows the frequency (%) of positive Lyme borreliosis sera in the early stages of Lyme borreliosis found by the above-described peptide and $rOspC_{fl}$ ELISAs, respectively.

TABLE 2

| Patient sera | $rOspC_{fl}$ ELISA | Peptide ELISA |
|---|---|---|
| EM (n = 80) | n = 45 (43.8%) | n = 26 (32.5%) |
| NB (n = 101) | n = 49 (48.5%) | n = 46 (45.5%) |
| Early Lyme borreliosis (EM and NB) (n = 181) | n = 94 (46.4%) | n = 72 (39.8%) |

First of all, it can be concluded that the use of $rOspC_{fl}$ instead of $rOspC_t$ improves the immunological sensitivity of the recombinant ELISA, thereby confirming the suspicion that the C-terminus of OspC is essential in the immunological recognition of OspC in humans.

Figure 2:
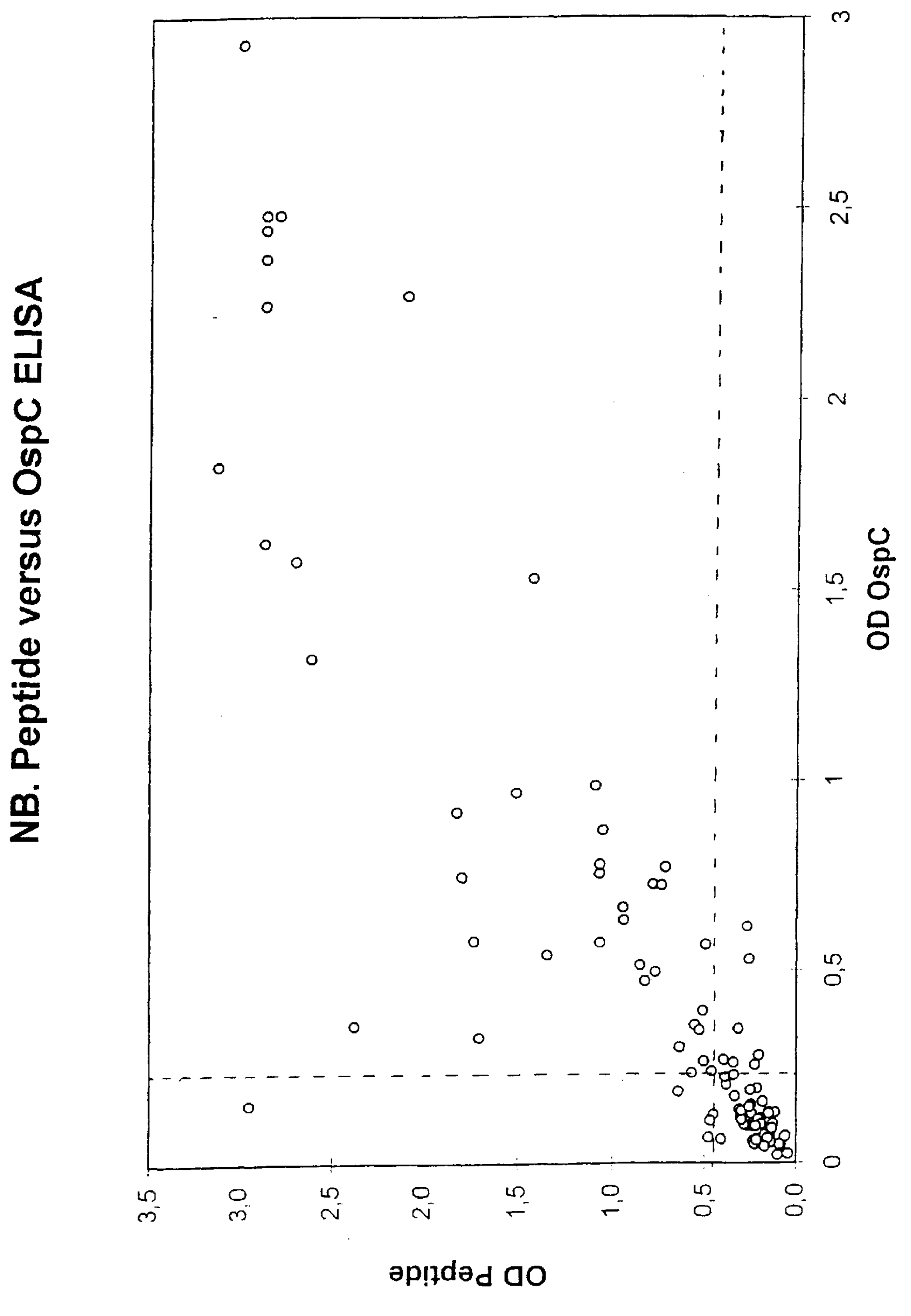
Figure 3:
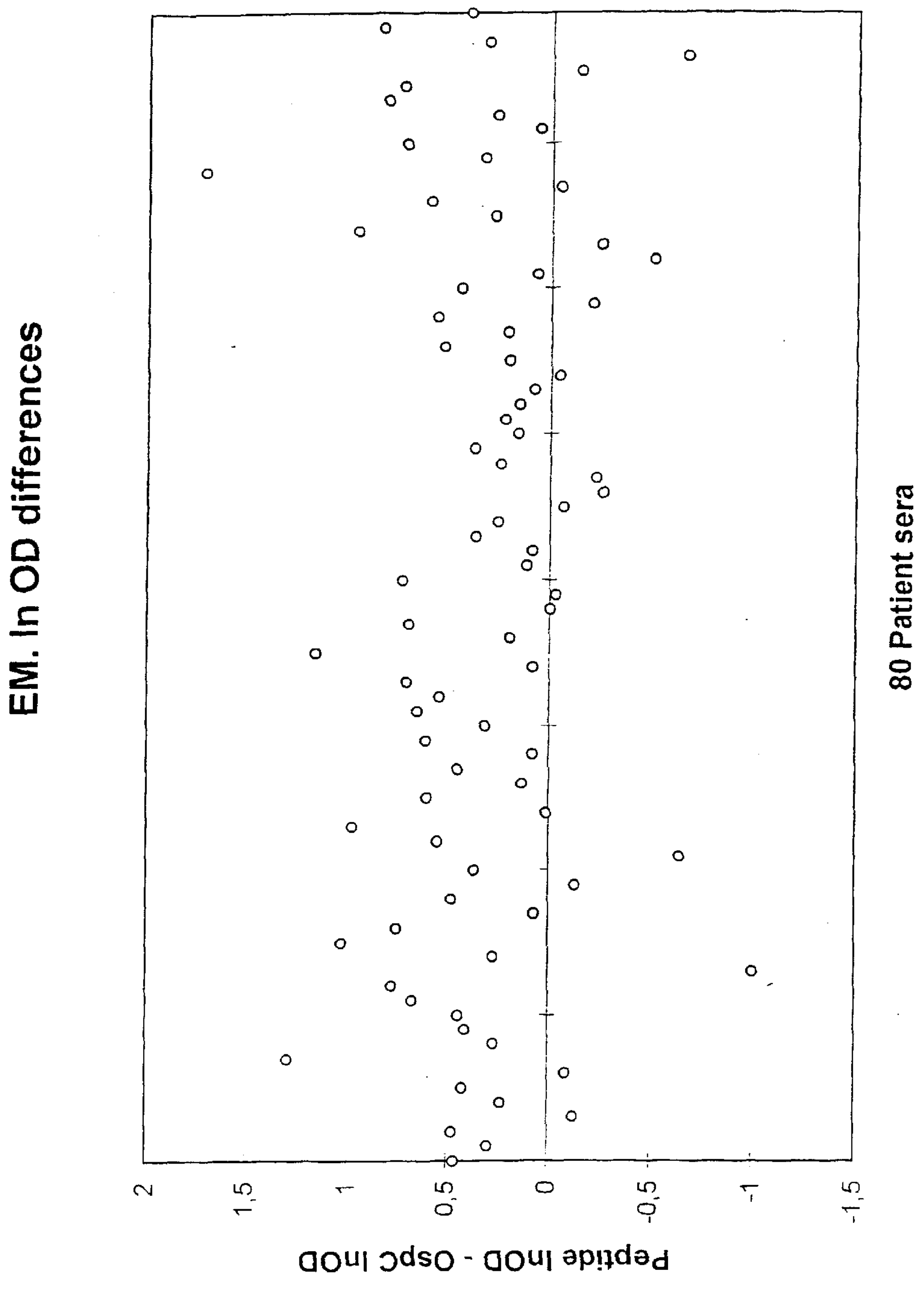
Figure 4:
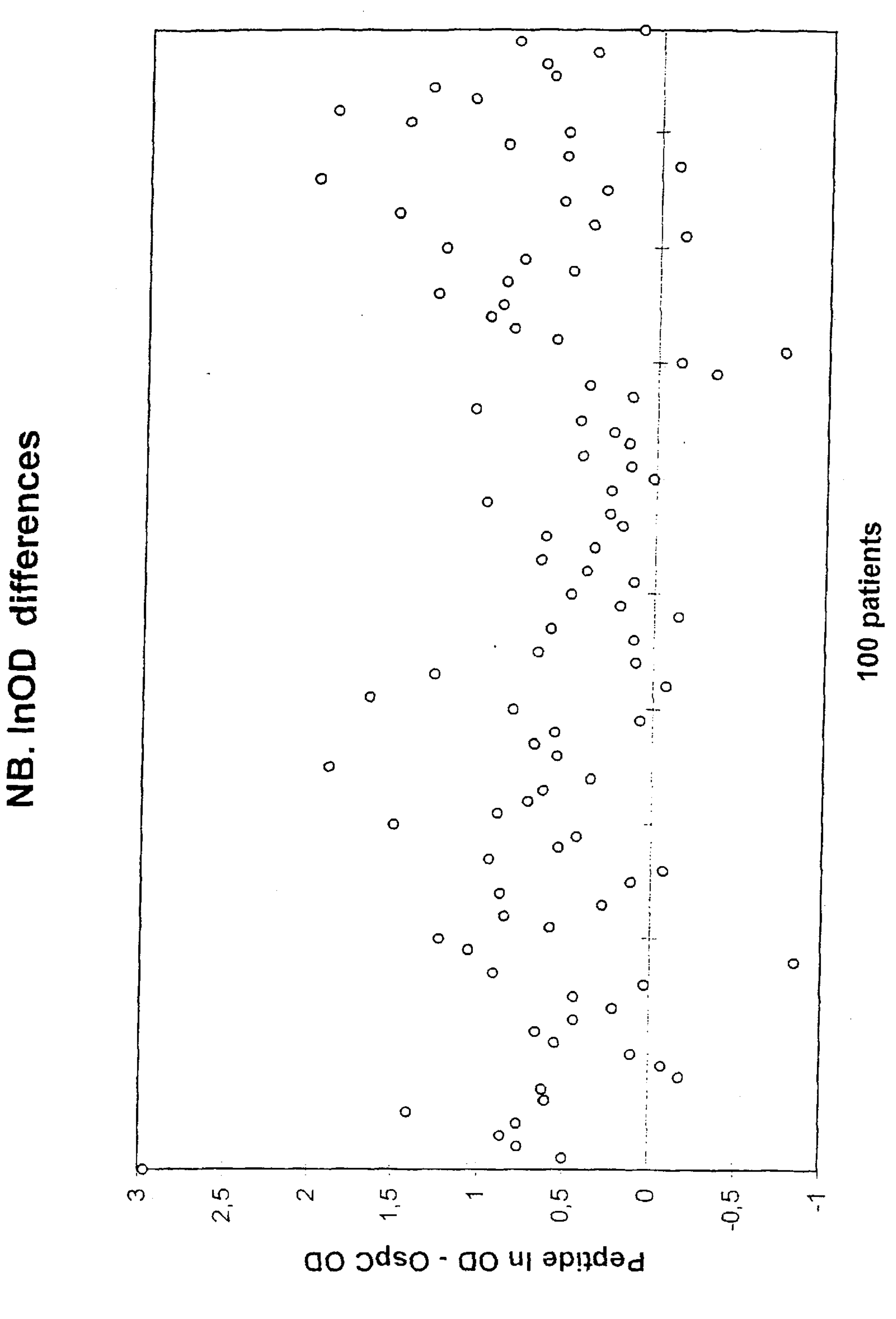

FIGS. 1 and 2 compare the individual results obtained in patients with Erythema Migrans (EM) and neuroborelliosis (NB), respectively, the first two stages of Lyme borreliosis regarding the quantitative measurement of IgM in the peptide ELISA and the $rOspC_{fl}$ ELISA. The horizontal and vertical broken lines mark the 98% specific diagnostic cut-off levels for the respective peptide and rOspC ELISA (0.460 and 0.230, respectively). As can be seen, the OD titer is significantly higher for the peptide ELISA. This is also evident from FIGS. 3 and 4 which show the difference of logarithmized OD values from the two assays in the two groups of patients.

It can be concluded that in this setup, the sensitivity of the peptide ELISA is approximately 86% of the $rOspC_{fl}$ ELISA in detecting early Lyme borreliosis (stage 1 and 2). This is a surprisingly high sensitivity, bearing in mind that the antigenic diversity in the C-terminus of OspC is considerable (a number of serotypes are known which e.g. have other amino acids than serine in the 6th position in SEQ ID NO: 1) and that full-length OspC comprises a much higher number of epitopes than the decapeptide employed in the present peptide ELISA.

Further, since the OD cutoff-value in the peptide ELISA currently is as high as 0.460. It is expected that a fine-tuning of the assay with respect to the concentration of reagents (especially streptavidin) will lead to a decrease in the cutoff-value. Further, since human antibodies against avidin have been reported, it is possible that human anti-bodies may react with streptavidin and therefore a change of the linking system or an efficient block of the streptavidin are both possibilities which will be exploited. It is also the plan to expand the panel of sera from healthy blood donors in order to provide a better statistical basis for the assessment of the cutoff value; at present there might be individuals in the donor group which have been sensitized with OspC, and these will of course have an effect on the assessment of the cutoff-value which will be higher than had the negative controls been truly negative.

Figure 5:
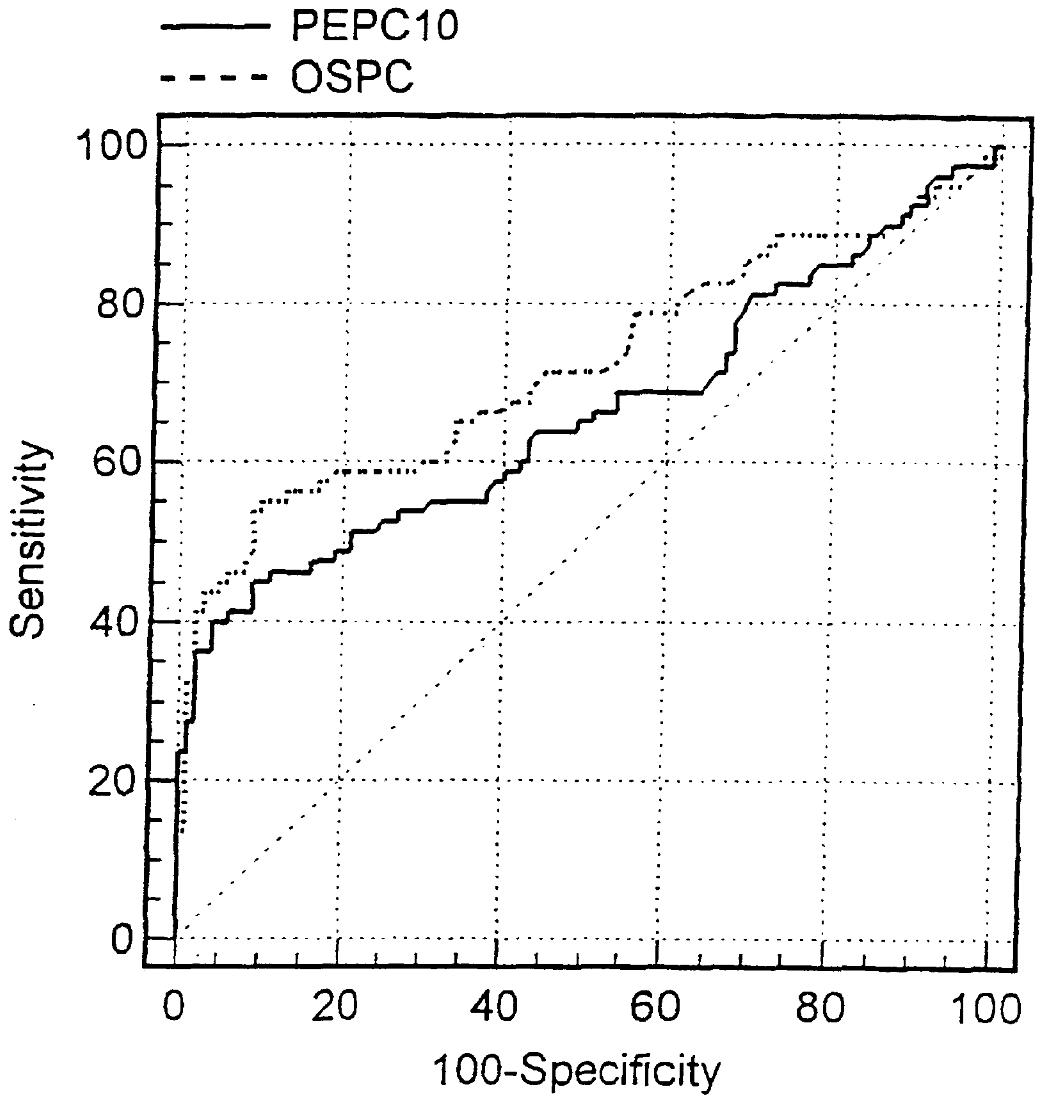
Figure 6:
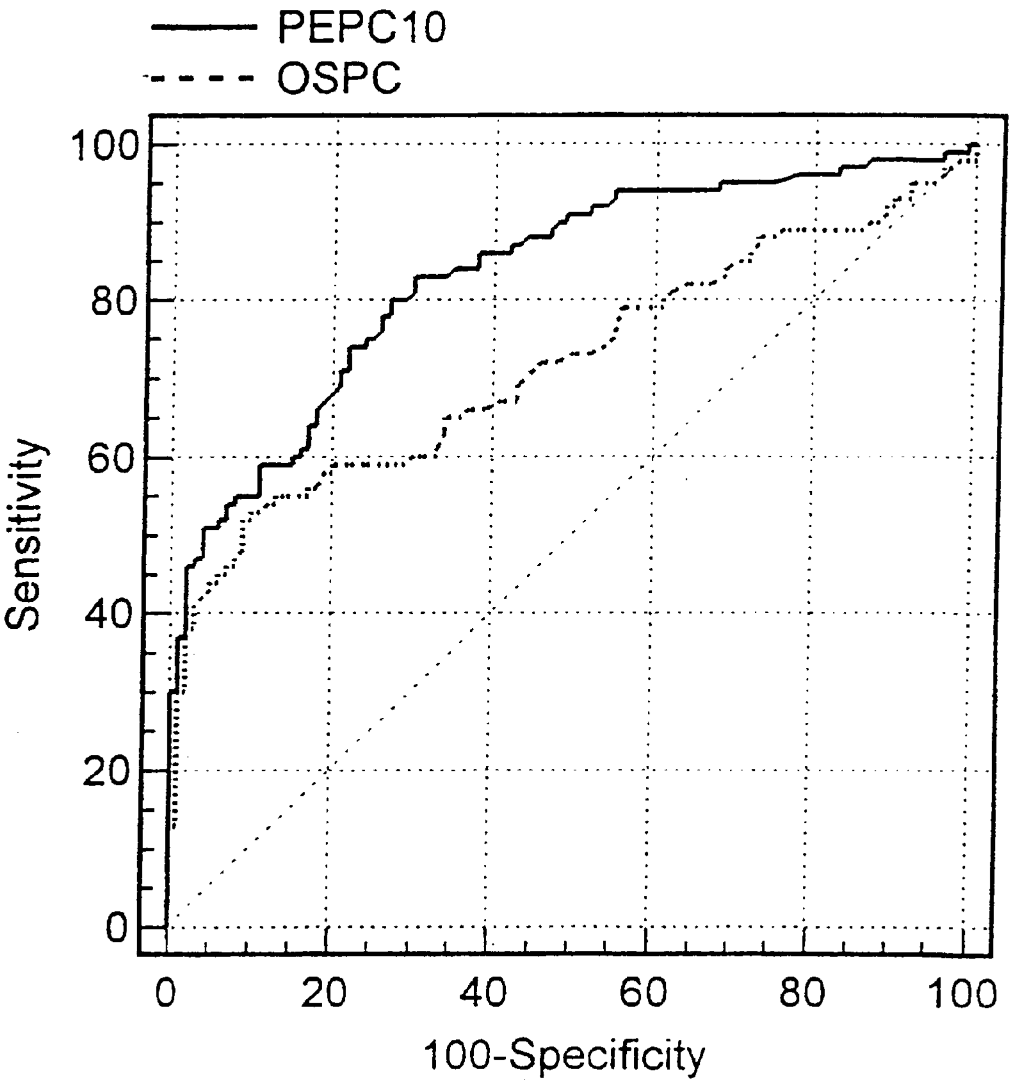

Finally, in FIGS. 5 and 6 are shown ROC plots comparing the accuracy of the peptide ELISA and of the $rOspC_{fl}$ ELISA in patients suffering from EM and NB, respectively. The ROC plots provide a pure index of accuracy by demonstrating graphically the entire spectrum of sensitivity/specificity pairs for a particular test. A decision threshold must be chosen for a test to be used in patient care but there is no need to choose any particular decision threshold for assessing accuracy. The ROC graph is a plot of all of the sensitivity/specificity pairs resulting from continuously varying the decision threshold over the entire range of results observed. On the y-axis is sensitivity plotted and on the x-axis is the false positive fraction (or 1-specificity) plotted. A plot lying above and to the left of another plot indicates greater observed accuracy. A review of use of ROC plots can be seen in Zweig and Campbell (1993).

The result which is apparent from FIGS. 5 and 6 is that the peptide ELISA is more accurate in patients suffering from NB whereas the opposite is the case for EM patients.

(It should be noted that an ELISA using direct coating of microtiter plates with C-terminal OspC fragments was also set up, using precisely the same conditions as the rOspC ELISA described above, including a coating concentration of the peptide fragments of 0.4 μg/ml. The results did, however, coincide with the results reported in this example, demonstrating that the specific conditions used in the ELISA are not crucial).

Effect of Combining the Flagellum Assay with the rOspC ELISA and the Peptide ELISA.

From the results listed in the following table (Table 3), it is evident that a significant number of patients revealed either a sole anti-rOspC or a sole anti-flagellum antibody response. The overall diagnostic sensitivity for IgM increased by 15% when adding the $rOspC_{fl}$ ELISA results to the flagellum ELISA results in the first stage of Lyme borreliosis (erythema migrans, EM) and by 12% in second stage of Lyme borreliosis (neuroborreliosis, NB). When adding the peptide ELISA results, the overall sensitivity for IgM was increased by 7.5% and 12% in the first and second stages, respectively.

TABLE 3

| Comparing the IgM rOspC$_{fl}$ and IgM decapeptide ELISA results with the IgM flagellum ELISA results in the early stages of *Lyme borreliosis* | | |
|---|---|---|
| The first stage of *Lyme borreliosis* (EM), n = 80 | Flagellum IgM negative n = 50 (62.5%) | Flagellum IgM positive n = 30 (37.5%) |
| rOspC$_{fl}$ IgM negative n = 45 (56.25%) | n = 38 (47.50%) | n = 7 (8.75%) |
| rOspC$_{fl}$ IgM positive n = 35 (43.75%) | n = 12 (15.00%) | n = 23 (28.75%) |
| Peptide IgM negative n = 54 (67.5%) | n = 44 (55.00%) | n = 10 (12.50) |
| Peptide IgM positive n = 26 (32.5%) | n = 6 (7.50%) | n = 20 (25.00%) |
| The second stage of *Lyme borreliosis* (NB), n = 101 | Flagellum IgM negative n = 37 (36.6%) | Flagellum IgM positive n = 63 (62.4%) |
| rOspC$_{fl}$ IgM negative n = 52 (51.5%) | n = 25 (24.75%) | n = 26 (25.74%) |
| rOspC$_{fl}$ IgM positive n = 49 (48.5%) | n = 12 (11.88%) | n = 37 (36.63%) |
| Decapeptide IgM negative n = 55 (54.5%) | n = 25 (24.75%) | n = 30 (29.70%) |
| Decapeptide IgM positive n = 46 (45.5%) | n = 12 (11.88%) | n = 33 (32.67%) |

In the third stage of Lyme borreliosis (ACA), the prevalence of anti-ospC was low and did not add significantly to the overall sensitivity (data not shown).

Conclusion: The combined use of an rOspC ELISA and the flagellum ELISA improves the overall diagnostic sensitivity in IgM serodiagnosis of early Lyme borreliosis. This is also true for the peptide ELISA, although to a smaller extent in the present setup. As discussed above, however, it is expected that the peptide ELISA will be fine-tuned and thereby obtain a higher sensitivity than the present.

It should be noted that an attempt to add the IgG rOspC ELISA results to the results from a commercially available IgG flagellum ELISA gave no significant improvement, properly due to a lack of IgG reactive with OspC.

Example 3

Development and Testing of Analogues of the Decapeptide having SEQ ID NO: 1

Having demonstrated that a short OspC derived C-terminal decapeptide comprises an essential epitope, it is important to identify the location and precise nature of the epitope.

Therefore, a set of experiments have been carried out where the ability have been tested of a number of analogues of the C-terminus of SEQ ID NO: 3 to inhibit the immune reactivity between rOspC$_{fl}$ and selected antisera in an ELISA. More specifically, the ability of the various analogues to inhibit the binding of polyclonal anti-OspC antibodies in solution was examined in sera from LB patients to rOspC-coated ELISA plates.

The immunoreactivity to OspC was specified by using six randomly selected NB sera with an OD>1.5 in the IgM rOspC ELISA. The respective serum dilutions were determined, based on a serum dilution curve obtained in the IgM rOspC ELISA, for each of the six sera. The highest dilution, which still achieved the maximal OD value was used. 5 sera were diluted 1:200, and one serum 1:1000. The sera were diluted in the buffer used for the IgM rOspC ELISAs.

The affinity of the OspC derivatives was measured by incubation of each of the six sera with the respective OspC derivatives at 10 different dilutions (covering a two-fold range) overnight at 4° C. The rOspC ELISA was then performed as described previously, in order to determine the effect of the IgM binding to OspC.

In this setup, the following experiments were performed:

Importance of Length of the C-terminal Fragment of OspC 10 overlapping peptides corresponding to the carboxy-terminal 4, 5, 6, 7, 8, 9, 10, 15, and 20 amino acids of OspC, were also tested in order to determine the importance of the length of the C-terminal epitope for the affinity to OspC antibodies. The following fragments were thus synthesized:

$NH_2$-LTNSVKELTNPVVAESPKKP-COOH (SEQ ID NO: 15), $NH_2$-KELTNPVVAESPKKP-COOH (SEQ ID NO: 16), $NH_2$-PVVAESPKKP-COOH (SEQ ID NO: 1), $NH_2$-VVAESPKKP-COOH (SEQ ID NO: 17), $NH_2$-VAESPKKP-COOH (SEQ ID NO: 18), $NH_2$-AESPKKP-COOH (SEQ ID NO: 19), $NH_2$-ESPKKP-COOH (SEQ ID NO: 20), $NH_2$-SPKKP-COOH (SEQ ID NO: 21), and $NH_2$-PKKP-COOH (SEQ ID NO: 22).

The inhibition experiments using fragments of differing lengths gave as a result that all but the 4-mer PKKP (SEQ ID NO: 22) was able to inhibit binding between rOspC$_{fl}$ and antibodies in 5 of 6 patient sera (one single serum could, however, be inhibited by the 4-mer). One of the sera could not be inhibited at all, and was thus excluded in the following tests.

The conclusion is thus, that the peptide must have a length of at least 5 amino acid residues to be effective in binding to the OspC specific antibodies in human sera.

Alanine Scan of the C-terminus of OspC 10 different OspC fragments were used in this set of experiments:

$NH_2$-PVVAESPKKA-COOH (SEQ ID NO: 23), $NH_2$-PVVAESPKAP-COOH (SEQ ID NO: 24), $NH_2$-PVVAESPAKP-COOH (SEQ ID NO: 25), $NH_2$-PVVAESAKKP-COOH (SEQ ID NO: 26), $NH_2$-PVVAEAPKKP-COOH (SEQ ID NO: 27), $NH_2$-PVVAASPKKP-COOH (SEQ ID NO: 28), $NH_2$-PVVFESPKKP-COOH (SEQ ID NO: 29), $NH_2$-PVAAESPKKP-COOH (SEQ ID NO: 30), $NH_2$-PAVAESPKKP-COOH (SEQ ID NO: 31), and $NH_2$-AVVAESPKKP-COOH (SEQ ID NO: 32).

These 10 analogues of the native C-terminal decamer of OspC, where each amino acid residue is individually replaced by L-alanine (except for the substitution of the native alanine in the 4 position of SEQ ID NO: 1 with phenylalanine), were used for a systematic study in order to evaluate the role for antigenicity of a particular residue in the peptide. This technique is termed an "alanine-scan". L-alanine is used as substitute in the analogues, since thereby the significance of each side chain can be evaluated.

It is assumed that single substitutions by L-alanine do not disturb the secondary structure or change the hydrophobicity. Therefore it is possible to study the role of the side chain functional groups for the affinity to antibodies.

The alanine scan gave the following results: Decapeptide analogues of SEQ ID NO: 1 having a single alanine substitution in residue 1, 2, 3, 4 (substituted with phenylalanine), 5, or 6 of SEQ ID NO: 1 were all capable of inhibiting binding between $rOspC_{fl}$ and the 5 antisera. Alanine substitutions in the remaining 4 residues resulted in peptides having no or reduced effect on the immune reactivity between the 5 antisera and $rOspC_{fl}$ (peptides with alanine substitution in residues 7, 8, 9, and 10 could inhibit binding with 1, 3, 1, and 0 sera, respectively).

Hence, the sequence of the 4 C-terminal amino acids in OspC seems to be essential for immune recognition between positive sera and OspC and it seems that the presence of the C-terminal proline residue is essential with respect to the presence of a ring structure similar to that of proline.

Importance of the Carboxy Group in the C-terminal Proline

One variant ($NH_2$-PVVAESPKKP-$CONH_2$ (SEQ ID NO: 33)) of the C-terminal decamer of OspC, wherein the carboxyl group was replaced by an amino group, was also tested in the setup.

This amidated peptide was incapable of inhibiting binding between $rOspC_{fl}$ and the 5 antisera. Hence, apart from the importance of the presence of a proline-like structure, a carboxy function also seems essential in the C-terminus.

Evaluation of unusual Amino Acid Substitutions

In order to further elucidate the importance of single amino acid residues in the C-terminus, a number of substitution analogues were prepared. These analogues had the general formulas $NH_2$-PVVAESPK#P-COOH (SEQ ID NO: 34), $NH_2$-PVVAES*KKP-COOH (SEQ ID NO: 35), and $NH_2$-¤KKP-COOH (SEQ ID NO: 36), wherein

* designates L-hydroxyproline, 1,2,3,4-L-tetrahydroisoquinoline-3-carboxylic acid, L-thiazolidine-4-carboxylic acid, homoproline, and D-proline;

\# designates L-diaminopropionic acid, diaminoacetic acid, L-diaminobutyric acid, L-ornithine, D-arginine, and D-lysine; and.

¤ designates L-indoline-2-carboxylic acid.

The use of unusual amino acid residues as substituents in SEQ ID NO: 1 gave as a result that only one peptide where the proline in position 7 was substituted with an L-thiazolidine-4-carboxylic acid residue was able to inhibit the test system in all 5 sera. This amino acid residue resembles proline but has an —S— group instead of an —$CH_2$— group in the 4-position of the ring structure and is hence slightly more polar than proline.

It thus seems that the polarity of residue 7 in SEQ ID NO: 1 is relatively unimportant whereas the presence of the ring structure (or at least of the rigid "bend" in the peptide chain introduced thereby) is essential, in view of the impact on immune reactivity of an alanine substitution in this residue.

In general it must be concluded that substitutions of the 5 C-terminal amino acids of OspC has a negative impact on the diagnostic utility, but it must also be concluded that certain substitutions with very similar amino acids are possible without negatively affecting the diagnostic utility of the C-terminal peptide.

It should finally be mentioned that one test serum exhibited reactivity with a large number of the tested analogues.

Other Substituted Analogues

The analogues $NH_2$-PVVPESPKKP-COOH (SEQ ID NO: 37), $NH_2$-PVVAESPKNP-COOH (SEQ ID NO: 38), and $NH_2$-PPPPESPKKP-COOH (SEQ ID NO: 39) were synthesized and tested in order to investigate whether i.a. a proline helix structure is an important feature of the epitopic region and to investigate the importance of the lysine residue in position 9 of SEQ ID NO: 1.

The results obtained are shown in the following table:

| | PVVPESPKKP (SEQ ID NO: 37) | PPPPESPKKP (SEQ ID NO: 39) | PVVAESPKNP (SEQ ID NO: 38) |
|---|---|---|---|
| Serum 1 | 70% inhibition | 70% inhibition | 50% inhibition |
| Serum 2 | 100% inhibition | 100% inhibition | 0% inhibition |
| Serum 3 | 100% inhibition | 100% inhibition | 0% inhibition |
| Serum 4 | 0% inhibition | 0% inhibition | 0% inhibition |
| Serum 5 | 40% inhibition | 40% inhibition | 0% inhibition |

The conclusion is that the immune reactivity of all 3 peptides is reduced compared to the peptide having SEQ ID NO: 1. It is further established that the nature of the first 5 residues of SEQ ID NO: 1 is less important than the nature of the last 5 residues, since the peptide PPPPESPKKP (SEQ ID NO: 39) retains a high degree of reactivity with the antisera, in spite of the fact that this peptide has a sequence identity with SEQ ID NO: 1 of only 70% (and that the first 5 residues are only 40% identical to the first 5 residues in SEQ ID NO: 1).

Furthermore, the importance for immune reactivity of the sequence PKKP (SEQ ID NO: 22) in the C-terminus is once again established by the negative effect of the substitution of the 9-lys with a 9-Asn. Based on this finding, it would seem that residue 9 of SEQ ID NO: 1 should be positively charged and/or have a long side-chain in order for the peptide to retain its immune reactivity with the test sera. To investigate this further, 9-lys was substituted with 9-arg and tested, and in spite of the charged nature of the side-chain in the arginine and the length of this side-chain, this variant exhibited no effect in the inhibition assay. The lysine in the 9 position of SEQ ID NO: 1 thus also seems to be essential.

It should be noted that naturally occurring variants of OspC exist which have asparagine in the residue corresponding to 9-lys in SEQ ID NO: 1. Consequently, it is possible that none of the test sera have been raised against this OspC variant and this renders it more likely that a diagnostic agent for global use should also include peptides having the C-terminal sequence PKNP. This should result in the "capture" of more seropositives against OspC than a "single antigen agent".

Example 4

Western Blot Utilizing the Decapeptide having SEQ ID NO: 1

In preliminary experiments, it has been documented that the peptide having SEQ ID NO: 1 can be used as a serodiagnostic test antigen in western blot by adding 10 μg of the peptide in PBS buffer to a nitrocellulose (NC) membrane, blocking overnight in TRIS buffered saline with 1% BSA, washing 3 times in TRIS buffered saline with Tween, and incubation for two hours at room temperature with serum from a patient with established neuroborreliosis (diluted 1:100 in TRIS buffered saline with 1% BSA). After three further washes in TRIS buffered saline with Tween, antibody reactive peptide was detected with alkaline phosphatase-coupled rabbit anti-human immune globulin M (DAKO, Denmark; cat. no. 337). The conjugate was diluted 1:1000 in TRIS buffered saline with 1% BSA and the NC membrane was incubated with colour substrate (BCIP and NBT; 1:500) for 10 minutes.

Example 5

Use of the C-terminal Peptide in a Vaccinating Agent

Two different observations have suggested that it may prove difficult to induce high titer IgG antibodies to the C-terminal region. Firstly, it has been found that only few Lyme borreliosis sera comprise IgG antibodies to the C-terminal decapeptide, and secondly, rabbits immunized with gel-purified native OspC in Freunds complete adjuvant did not produce antibodies to the C-terminal region (data not shown). This latter observation supports the hypothesis that the spatial organization of OspC in the outer membrane is intimately linked to the specificity of naturally occurring antibody. Thus, for vaccine development purposes it is proposed that the C-terminal B-cell epitope should be coupled to a strong T-cell epitope. This epitope could be of any relevant origin, for example selected among known *B. burgdorferi* antigens or the secreted antigens from *Mycobacterium tuberculosis* (PPD), in order to induce a high-titered long-lasting protective antibody response.

Presently, it is planned to fuse the decapeptide having SEQ ID NO: 1 in the N-terminus to a peptide comprising a known T-cell epitope from the *M. tuberculosis* antigen ESAT-6 (Brandt et al. (1996) discloses two such T-cell epitopes). The resulting fusion peptide will be e.g. 25 amino acid residues in length and will be formulated and administered as described above in the present specification.

LIST OF REFERENCES

Altman D. G., Practical statistics for medical research, 1. ed. 1991 (textbook)

Brandt et al. (1996), J. Immunol. 157: 3527–3533

Current Protocols in Immunology (1995), John Wiley and sons, Inc.

Fung B. P. et al. (1994), Infect. and Immun. 62: 3213–3221.

Gerber M. A. et al. (1995), J. Infect. Dis. 171: 724–7.

Hansen K. et al. (1991), J. Clin. Microbiol. 29: 166–173.

Hansen K. et al. (1988), J. Clin. Microbiol. 26: 338–346.

Holm, A. and Meldal, M. (1989), Multiple column peptide synthesis, p. 208E, Bayer and G. Jung (ed.), Peptides 1988, Walter de Gruyter & Co. Berlin-N.Y.

Meldal, M et al. (1993), Multiple Column peptide synthesis, Part 2, Int. J. Peptide & Protein Res. 41: 250–260.

Merrifield (1969). Advan. Enzymol. 32: 221

Padula S. J. et al. (1994), J. Clin. Microbiol. 32: 1733–1738.

The QIAexpressionist. 2nd Edition. KEBO lab. Joanne Crowe, QIAGEN Inc. and Karsten Henco, DIAGEN GmbH.

Ulmer J B et al. (1993), Curr. Opin. Invest. Drugs, 2: 983–989.

Wilske B. et al. (1994), Med. Microbiol. Immunol. 183: 43–59.

Zweig, M. H. and Campbell G. (1993), Clin. Chem. 39: 561–577.

SEQUENCE LISTING

```
<160> NUMBER OF SEQ ID NOS: 43

<210> SEQ ID NO 1
<211> LENGTH: 10
<212> TYPE: PRT
<213> ORGANISM: Borrelia garinii
<220> FEATURE:
<221> NAME/KEY: misc_feature
<223> OTHER INFORMATION: FRAGMENT TYPE: C-terminal; STRAIN: DK6,
      INDIVIDUAL ISOLATE: BN1068

<400> SEQUENCE: 1

Pro Val Val Ala Glu Ser Pro Lys Lys Pro
1               5                   10


<210> SEQ ID NO 2
<211> LENGTH: 630
<212> TYPE: DNA
<213> ORGANISM: Borrelia garinii
<220> FEATURE:
<221> NAME/KEY: misc_feature
<223> OTHER INFORMATION: MOLECULE TYPE: DNA (genomic); STRAIN: DK6;
      INDIVIDUAL ISOLATE: BN1068
<220> FEATURE:
<221> NAME/KEY: CDS
<222> LOCATION: (10)..(630)

<400> SEQUENCE: 2

cacaaatta atg aaa aag aat aca tta agt gcg ata tta atg act tta ttt      51
          Met Lys Lys Asn Thr Leu Ser Ala Ile Leu Met Thr Leu Phe
          1               5                   10

tta ttt ata tct tgt aat aat tca ggt ggg gat tct gca tct act aat        99
Leu Phe Ile Ser Cys Asn Asn Ser Gly Gly Asp Ser Ala Ser Thr Asn
15                  20                  25                  30
```

-continued

```
cct gat gag tct gca aaa gga cct aat ctt acc gta ata agc aaa aaa      147
Pro Asp Glu Ser Ala Lys Gly Pro Asn Leu Thr Val Ile Ser Lys Lys
                35                  40                  45

att aca gat tct aat gca ttt tta ctg gct gtg aaa gaa gtt gag gct      195
Ile Thr Asp Ser Asn Ala Phe Leu Leu Ala Val Lys Glu Val Glu Ala
            50                  55                  60

ttg ctt tca tct ata gat gaa ctt tct aaa gct att ggt aaa aaa ata      243
Leu Leu Ser Ser Ile Asp Glu Leu Ser Lys Ala Ile Gly Lys Lys Ile
        65                  70                  75

aaa aat gat ggt act tta gat aac gaa gca aat cga aac gaa tca ttg      291
Lys Asn Asp Gly Thr Leu Asp Asn Glu Ala Asn Arg Asn Glu Ser Leu
    80                  85                  90

ata gca gga gct tat gaa ata tca aaa cta ata aca caa aaa tta agt      339
Ile Ala Gly Ala Tyr Glu Ile Ser Lys Leu Ile Thr Gln Lys Leu Ser
95                  100                 105                 110

gta ttg aat tca gaa gaa tta aag gaa aaa att aaa gag gct aag gat      387
Val Leu Asn Ser Glu Glu Leu Lys Glu Lys Ile Lys Glu Ala Lys Asp
                115                 120                 125

tgt tcc gaa aaa ttt act act aag cta aaa gat agt cat gca gag ctt      435
Cys Ser Glu Lys Phe Thr Thr Lys Leu Lys Asp Ser His Ala Glu Leu
            130                 135                 140

ggt ata caa agc gtt cag gat gat aat gca aaa aaa gct att tta aaa      483
Gly Ile Gln Ser Val Gln Asp Asp Asn Ala Lys Lys Ala Ile Leu Lys
        145                 150                 155

aca cat gga act aaa gac aag ggt gct aaa gaa ctt gaa gag tta ttt      531
Thr His Gly Thr Lys Asp Lys Gly Ala Lys Glu Leu Glu Glu Leu Phe
    160                 165                 170

aaa tca cta gaa agc ttg tca aaa gca gcg caa gca gca tta act aat      579
Lys Ser Leu Glu Ser Leu Ser Lys Ala Ala Gln Ala Ala Leu Thr Asn
175                 180                 185                 190

tca gtt aaa gag ctt aca aat cct gtt gtg gca gaa agt cca aaa aaa      627
Ser Val Lys Glu Leu Thr Asn Pro Val Val Ala Glu Ser Pro Lys Lys
                195                 200                 205

cct                                                                  630
Pro

<210> SEQ ID NO 3
<211> LENGTH: 207
<212> TYPE: PRT
<213> ORGANISM: Borrelia garinii

<400> SEQUENCE: 3

Met Lys Lys Asn Thr Leu Ser Ala Ile Leu Met Thr Leu Phe Leu Phe
1               5                   10                  15

Ile Ser Cys Asn Asn Ser Gly Gly Asp Ser Ala Ser Thr Asn Pro Asp
            20                  25                  30

Glu Ser Ala Lys Gly Pro Asn Leu Thr Val Ile Ser Lys Lys Ile Thr
        35                  40                  45

Asp Ser Asn Ala Phe Leu Leu Ala Val Lys Glu Val Glu Ala Leu Leu
    50                  55                  60

Ser Ser Ile Asp Glu Leu Ser Lys Ala Ile Gly Lys Lys Ile Lys Asn
65                  70                  75                  80

Asp Gly Thr Leu Asp Asn Glu Ala Asn Arg Asn Glu Ser Leu Ile Ala
                85                  90                  95

Gly Ala Tyr Glu Ile Ser Lys Leu Ile Thr Gln Lys Leu Ser Val Leu
            100                 105                 110

Asn Ser Glu Glu Leu Lys Glu Lys Ile Lys Glu Ala Lys Asp Cys Ser
        115                 120                 125
```

-continued

```
Glu Lys Phe Thr Thr Lys Leu Lys Asp Ser His Ala Glu Leu Gly Ile
    130                 135                 140

Gln Ser Val Gln Asp Asp Asn Ala Lys Lys Ala Ile Leu Lys Thr His
145                 150                 155                 160

Gly Thr Lys Asp Lys Gly Ala Lys Glu Leu Glu Glu Leu Phe Lys Ser
                165                 170                 175

Leu Glu Ser Leu Ser Lys Ala Ala Gln Ala Ala Leu Thr Asn Ser Val
            180                 185                 190

Lys Glu Leu Thr Asn Pro Val Val Ala Glu Ser Pro Lys Lys Pro
        195                 200                 205


<210> SEQ ID NO 4
<211> LENGTH: 642
<212> TYPE: DNA
<213> ORGANISM: Borrelia burgdorferi sensu stricto
<220> FEATURE:
<221> NAME/KEY: misc_feature
<223> OTHER INFORMATION: MOLECULE TYPE: DNA (genomic); STRAIN: DK7;
      INDIVIDUAL ISOLATE: BN1067
<220> FEATURE:
<221> NAME/KEY: CDS
<222> LOCATION: (10)..(642)

<400> SEQUENCE: 4

cacaaatta atg aaa aag aat act tta agt gca ata tta atg act tta ttt      51
          Met Lys Lys Asn Thr Leu Ser Ala Ile Leu Met Thr Leu Phe
          1               5                   10

tta ttt ata tct tgt aat aat tca gga aaa gat ggg aat aca tct gca       99
Leu Phe Ile Ser Cys Asn Asn Ser Gly Lys Asp Gly Asn Thr Ser Ala
15                  20                  25                  30

aat tct gct gat gag tct gtt aaa ggg cct aat ctt aca gaa ata agt      147
Asn Ser Ala Asp Glu Ser Val Lys Gly Pro Asn Leu Thr Glu Ile Ser
                35                  40                  45

aaa aaa att acg gat tct aat gcg gtt tta ctt gct gtg aaa gag gtt      195
Lys Lys Ile Thr Asp Ser Asn Ala Val Leu Leu Ala Val Lys Glu Val
            50                  55                  60

gaa gcg ttg ctg tca tct ata gat gag ctt gct aaa gct att ggt aaa      243
Glu Ala Leu Leu Ser Ser Ile Asp Glu Leu Ala Lys Ala Ile Gly Lys
        65                  70                  75

aaa ata aaa aac gat ggt agt tta ggt gat gaa gca aat cac aac gag      291
Lys Ile Lys Asn Asp Gly Ser Leu Gly Asp Glu Ala Asn His Asn Glu
    80                  85                  90

tca ttg tta gca gga gct tat aca ata tca acc tta ata aca caa aaa      339
Ser Leu Leu Ala Gly Ala Tyr Thr Ile Ser Thr Leu Ile Thr Gln Lys
95                  100                 105                 110

tta agt aaa tta aac gga tca gaa ggt tta aag gaa aag att gcc gca      387
Leu Ser Lys Leu Asn Gly Ser Glu Gly Leu Lys Glu Lys Ile Ala Ala
                115                 120                 125

gct aag aaa tgc tct gaa gag ttt agt act aaa cta aaa gat aat cat      435
Ala Lys Lys Cys Ser Glu Glu Phe Ser Thr Lys Leu Lys Asp Asn His
            130                 135                 140

gca cag ctt ggt ata cag ggc gtt act gat gaa aat gca aaa aaa gct      483
Ala Gln Leu Gly Ile Gln Gly Val Thr Asp Glu Asn Ala Lys Lys Ala
        145                 150                 155

att tta aaa gca aat gca gcg ggt aaa gat aag ggc gtt gaa gaa ctt      531
Ile Leu Lys Ala Asn Ala Ala Gly Lys Asp Lys Gly Val Glu Glu Leu
    160                 165                 170

gaa aag ttg tcc gga tca tta gaa agc tta tca aaa gca gct aaa gag      579
Glu Lys Leu Ser Gly Ser Leu Glu Ser Leu Ser Lys Ala Ala Lys Glu
175                 180                 185                 190

atg ctt gct aat tca gtt aaa gag ctt aca agt cct gtt gtg gta gaa      627
```

-continued

```
Met Leu Ala Asn Ser Val Lys Glu Leu Thr Ser Pro Val Val Val Glu
                195                 200                 205

agt cca aaa aaa cct                                                642
Ser Pro Lys Lys Pro
            210


<210> SEQ ID NO 5
<211> LENGTH: 211
<212> TYPE: PRT
<213> ORGANISM: Borrelia burgdorferi sensu stricto

<400> SEQUENCE: 5

Met Lys Lys Asn Thr Leu Ser Ala Ile Leu Met Thr Leu Phe Leu Phe
1               5                   10                  15

Ile Ser Cys Asn Asn Ser Gly Lys Asp Gly Asn Thr Ser Ala Asn Ser
            20                  25                  30

Ala Asp Glu Ser Val Lys Gly Pro Asn Leu Thr Glu Ile Ser Lys Lys
        35                  40                  45

Ile Thr Asp Ser Asn Ala Val Leu Leu Ala Val Lys Glu Val Glu Ala
    50                  55                  60

Leu Leu Ser Ser Ile Asp Glu Leu Ala Lys Ala Ile Gly Lys Lys Ile
65                  70                  75                  80

Lys Asn Asp Gly Ser Leu Gly Asp Glu Ala Asn His Asn Glu Ser Leu
                85                  90                  95

Leu Ala Gly Ala Tyr Thr Ile Ser Thr Leu Ile Thr Gln Lys Leu Ser
            100                 105                 110

Lys Leu Asn Gly Ser Glu Gly Leu Lys Glu Lys Ile Ala Ala Ala Lys
        115                 120                 125

Lys Cys Ser Glu Glu Phe Ser Thr Lys Leu Lys Asp Asn His Ala Gln
    130                 135                 140

Leu Gly Ile Gln Gly Val Thr Asp Glu Asn Ala Lys Lys Ala Ile Leu
145                 150                 155                 160

Lys Ala Asn Ala Ala Gly Lys Asp Lys Gly Val Glu Glu Leu Glu Lys
                165                 170                 175

Leu Ser Gly Ser Leu Glu Ser Leu Ser Lys Ala Ala Lys Glu Met Leu
            180                 185                 190

Ala Asn Ser Val Lys Glu Leu Thr Ser Pro Val Val Val Glu Ser Pro
        195                 200                 205

Lys Lys Pro
    210


<210> SEQ ID NO 6
<211> LENGTH: 645
<212> TYPE: DNA
<213> ORGANISM: Borrelia afzelii
<220> FEATURE:
<221> NAME/KEY: misc_feature
<223> OTHER INFORMATION: MOLECULE TYPE: DNA (genomic); STRAIN: DK26;
      INDIVIDUAL ISOLATE: BN1066
<220> FEATURE:
<221> NAME/KEY: CDS
<222> LOCATION: (10)..(645)

<400> SEQUENCE: 6

cacaaatta atg aaa aag aat aca tta agt gcg ata tta atg act tta ttt     51
          Met Lys Lys Asn Thr Leu Ser Ala Ile Leu Met Thr Leu Phe
          1               5                   10

tta ttt ata tct tgt aat aat tca ggg aaa ggt ggg gat tct gca tct       99
Leu Phe Ile Ser Cys Asn Asn Ser Gly Lys Gly Gly Asp Ser Ala Ser
15                  20                  25                  30
```

-continued

```
act aat cct gct gac gag tct gcg aaa ggg cct aat ctt aca gaa ata      147
Thr Asn Pro Ala Asp Glu Ser Ala Lys Gly Pro Asn Leu Thr Glu Ile
                35                  40                  45

agc aaa aaa att aca gat tct aat gca ttt gta ctt gct gtt aaa gaa      195
Ser Lys Lys Ile Thr Asp Ser Asn Ala Phe Val Leu Ala Val Lys Glu
            50                  55                  60

gtt gag act ttg gtt tta tct ata gat gaa ctt gct aag aaa gct att      243
Val Glu Thr Leu Val Leu Ser Ile Asp Glu Leu Ala Lys Lys Ala Ile
        65                  70                  75

ggt caa aaa ata gac aat aat aat ggt tta gct gct tta aat aat cag      291
Gly Gln Lys Ile Asp Asn Asn Asn Gly Leu Ala Ala Leu Asn Asn Gln
    80                  85                  90

aat gga tcg ttg tta gca gga gcc tat gca ata tca acc cta ata aca      339
Asn Gly Ser Leu Leu Ala Gly Ala Tyr Ala Ile Ser Thr Leu Ile Thr
95                  100                 105                 110

gaa aaa ttg agt aaa ttg aaa aat tta gaa gaa tta aag aca gaa att      387
Glu Lys Leu Ser Lys Leu Lys Asn Leu Glu Glu Leu Lys Thr Glu Ile
                115                 120                 125

gca aag gct aag aaa tgt tcc gaa gaa ttt act aat aaa cta aaa agt      435
Ala Lys Ala Lys Lys Cys Ser Glu Glu Phe Thr Asn Lys Leu Lys Ser
            130                 135                 140

ggt cat gca gat ctt ggc aaa cag gat gct acc gat gat cat gca aaa      483
Gly His Ala Asp Leu Gly Lys Gln Asp Ala Thr Asp Asp His Ala Lys
        145                 150                 155

gca gct att tta aaa aca cat gca act acc gat aaa ggt gct aaa gaa      531
Ala Ala Ile Leu Lys Thr His Ala Thr Thr Asp Lys Gly Ala Lys Glu
    160                 165                 170

ttt aaa gat tta ttt gaa tca gta gaa ggc ttg tta aaa gca gct caa      579
Phe Lys Asp Leu Phe Glu Ser Val Glu Gly Leu Leu Lys Ala Ala Gln
175                 180                 185                 190

gta gca cta act aat tca gtt aaa gaa ctt aca agt cct gtt gta gca      627
Val Ala Leu Thr Asn Ser Val Lys Glu Leu Thr Ser Pro Val Val Ala
                195                 200                 205

gaa agt cca aaa aaa cct                                              645
Glu Ser Pro Lys Lys Pro
            210


<210> SEQ ID NO 7
<211> LENGTH: 212
<212> TYPE: PRT
<213> ORGANISM: Borrelia afzelii

<400> SEQUENCE: 7

Met Lys Lys Asn Thr Leu Ser Ala Ile Leu Met Thr Leu Phe Leu Phe
1               5                   10                  15

Ile Ser Cys Asn Asn Ser Gly Lys Gly Gly Asp Ser Ala Ser Thr Asn
            20                  25                  30

Pro Ala Asp Glu Ser Ala Lys Gly Pro Asn Leu Thr Glu Ile Ser Lys
        35                  40                  45

Lys Ile Thr Asp Ser Asn Ala Phe Val Leu Ala Val Lys Glu Val Glu
    50                  55                  60

Thr Leu Val Leu Ser Ile Asp Glu Leu Ala Lys Lys Ala Ile Gly Gln
65                  70                  75                  80

Lys Ile Asp Asn Asn Asn Gly Leu Ala Ala Leu Asn Asn Gln Asn Gly
                85                  90                  95

Ser Leu Leu Ala Gly Ala Tyr Ala Ile Ser Thr Leu Ile Thr Glu Lys
            100                 105                 110

Leu Ser Lys Leu Lys Asn Leu Glu Glu Leu Lys Thr Glu Ile Ala Lys
```

-continued

```
        115                 120                 125

Ala Lys Lys Cys Ser Glu Glu Phe Thr Asn Lys Leu Lys Ser Gly His
    130                 135                 140

Ala Asp Leu Gly Lys Gln Asp Ala Thr Asp Asp His Ala Lys Ala Ala
145                 150                 155                 160

Ile Leu Lys Thr His Ala Thr Thr Asp Lys Gly Ala Lys Glu Phe Lys
                165                 170                 175

Asp Leu Phe Glu Ser Val Glu Gly Leu Leu Lys Ala Ala Gln Val Ala
            180                 185                 190

Leu Thr Asn Ser Val Lys Glu Leu Thr Ser Pro Val Val Ala Glu Ser
        195                 200                 205

Pro Lys Lys Pro
    210


<210> SEQ ID NO 8
<211> LENGTH: 29
<212> TYPE: DNA
<213> ORGANISM: Artificial Sequence
<220> FEATURE:
<223> OTHER INFORMATION: Primer specific for B. garinii DK6: BF22

<400> SEQUENCE: 8

atagatatca ataattcagg tggggattc                                        29


<210> SEQ ID NO 9
<211> LENGTH: 33
<212> TYPE: DNA
<213> ORGANISM: Artificial Sequence
<220> FEATURE:
<223> OTHER INFORMATION: Primer specific for B. garinii DK6: BF65

<400> SEQUENCE: 9

tttgatatct caaggttttt ttggactttc tgc                                   33


<210> SEQ ID NO 10
<211> LENGTH: 35
<212> TYPE: DNA
<213> ORGANISM: Artificial Sequence
<220> FEATURE:
<223> OTHER INFORMATION: Primer specific for B. burgdorferi sensu
      stricto DK7: BF26

<400> SEQUENCE: 10

atagatatca ataattcagg aaaagatggg aatac                                 35


<210> SEQ ID NO 11
<211> LENGTH: 31
<212> TYPE: DNA
<213> ORGANISM: Artificial Sequence
<220> FEATURE:
<223> OTHER INFORMATION: Primer specific for B. afzelii DK26: BF24

<400> SEQUENCE: 11

atagatatca ataattcagg gaaaggtggg g                                     31


<210> SEQ ID NO 12
<211> LENGTH: 36
<212> TYPE: DNA
<213> ORGANISM: Artificial Sequence
<220> FEATURE:
<223> OTHER INFORMATION: Primer used for B. garinii DK6: BF22 and BF23

<400> SEQUENCE: 12
```

-continued

```
tttgatatct cacacaacag gatttgtaag ctcttt                          36


<210> SEQ ID NO 13
<211> LENGTH: 41
<212> TYPE: DNA
<213> ORGANISM: Artificial Sequence
<220> FEATURE:
<223> OTHER INFORMATION: Primer used for B. burgdorferi sensu stricto
      DK7: BF26 and BF27

<400> SEQUENCE: 13

tttgatatct cacacaacag actgtaagct cttaactgaa t                    41


<210> SEQ ID NO 14
<211> LENGTH: 42
<212> TYPE: DNA
<213> ORGANISM: Artificial Sequence
<220> FEATURE:
<223> OTHER INFORMATION: Primer used for B. afzelii DK26: BF24 and BF25

<400> SEQUENCE: 14

tttgatatct catacaacag gacttgtaag ttctttaact ga                   42


<210> SEQ ID NO 15
<211> LENGTH: 20
<212> TYPE: PRT
<213> ORGANISM: Artificial Sequence
<220> FEATURE:
<223> OTHER INFORMATION: One of the overlapping peptides corresponding
      to the carboxy-terminal of OspC that was tested in order to
      determine the importance of the length of the C-terminal epitope
      for the affinity to OspC antibodies

<400> SEQUENCE: 15

Leu Thr Asn Ser Val Lys Glu Leu Thr Asn Pro Val Val Ala Glu Ser
1               5                   10                  15
Pro Lys Lys Pro
            20


<210> SEQ ID NO 16
<211> LENGTH: 15
<212> TYPE: PRT
<213> ORGANISM: Artificial Sequence
<220> FEATURE:
<223> OTHER INFORMATION: One of the overlapping peptides corresponding
      to the carboxy-terminal of OspC that was tested in order to
      determine the importance of the length of the C-terminal epitope
      for the affinity to OspC antibodies

<400> SEQUENCE: 16

Lys Glu Leu Thr Asn Pro Val Val Ala Glu Ser Pro Lys Lys Pro
1               5                   10                  15


<210> SEQ ID NO 17
<211> LENGTH: 9
<212> TYPE: PRT
<213> ORGANISM: Artificial Sequence
<220> FEATURE:
<223> OTHER INFORMATION: One of the overlapping peptides corresponding
      to the carboxy-terminal of OspC that was tested in order to
      determine the importance of the length of the C-terminal epitope
      for the affinity to OspC antibodies

<400> SEQUENCE: 17

Val Val Ala Glu Ser Pro Lys Lys Pro
1               5


<210> SEQ ID NO 18
```

-continued

```
<211> LENGTH: 8
<212> TYPE: PRT
<213> ORGANISM: Artificial Sequence
<220> FEATURE:
<223> OTHER INFORMATION: One of the overlapping peptides corresponding
      to the carboxy-terminal of OspC that was tested in order to
      determine the importance of the length of the C-terminal epitope
      for the affinity to OspC antibodies

<400> SEQUENCE: 18

Val Ala Glu Ser Pro Lys Lys Pro
1               5


<210> SEQ ID NO 19
<211> LENGTH: 7
<212> TYPE: PRT
<213> ORGANISM: Artificial Sequence
<220> FEATURE:
<223> OTHER INFORMATION: One of the overlapping peptides corresponding
      to the carboxy-terminal of OspC that was tested in order to
      determine the importance of the length of the C-terminal epitope
      for the affinity to OspC antibodies

<400> SEQUENCE: 19

Ala Glu Ser Pro Lys Lys Pro
1               5


<210> SEQ ID NO 20
<211> LENGTH: 6
<212> TYPE: PRT
<213> ORGANISM: Artificial Sequence
<220> FEATURE:
<223> OTHER INFORMATION: One of the overlapping peptides corresponding
      to the carboxy-terminal of OspC that was tested in order to
      determine the importance of the length of the C-terminal epitope
      for the affinity to OspC antibodies

<400> SEQUENCE: 20

Glu Ser Pro Lys Lys Pro
1               5


<210> SEQ ID NO 21
<211> LENGTH: 5
<212> TYPE: PRT
<213> ORGANISM: Artificial Sequence
<220> FEATURE:
<223> OTHER INFORMATION: One of the overlapping peptides corresponding
      to the carboxy-terminal of OspC that was tested in order to
      determine the importance of the length of the C-terminal epitope
      for the affinity to OspC antibodies

<400> SEQUENCE: 21

Ser Pro Lys Lys Pro
1               5


<210> SEQ ID NO 22
<211> LENGTH: 4
<212> TYPE: PRT
<213> ORGANISM: Artificial Sequence
<220> FEATURE:
<223> OTHER INFORMATION: One of the overlapping peptides corresponding
      to the carboxy-terminal of OspC that was tested in order to
      determine the importance of the length of the C-terminal epitope
      for the affinity to OspC antibodies

<400> SEQUENCE: 22

Pro Lys Lys Pro
1
```

-continued

<210> SEQ ID NO 23
<211> LENGTH: 10
<212> TYPE: PRT
<213> ORGANISM: Artificial Sequence
<220> FEATURE:
<223> OTHER INFORMATION: One of the analogues of the native C-terminal decamer of OspC

<400> SEQUENCE: 23

Pro Val Val Ala Glu Ser Pro Lys Lys Ala
1 5 10

<210> SEQ ID NO 24
<211> LENGTH: 10
<212> TYPE: PRT
<213> ORGANISM: Artificial Sequence
<220> FEATURE:
<223> OTHER INFORMATION: One of the analogues of the native C-terminal decamer of OspC

<400> SEQUENCE: 24

Pro Val Val Ala Glu Ser Pro Lys Ala Pro
1 5 10

<210> SEQ ID NO 25
<211> LENGTH: 10
<212> TYPE: PRT
<213> ORGANISM: Artificial Sequence
<220> FEATURE:
<223> OTHER INFORMATION: One of the analogues of the native C-terminal decamer of OspC

<400> SEQUENCE: 25

Pro Val Val Ala Glu Ser Pro Ala Lys Pro
1 5 10

<210> SEQ ID NO 26
<211> LENGTH: 10
<212> TYPE: PRT
<213> ORGANISM: Artificial Sequence
<220> FEATURE:
<223> OTHER INFORMATION: One of the analogues of the native C-terminal decamer of OspC

<400> SEQUENCE: 26

Pro Val Val Ala Glu Ser Ala Lys Lys Pro
1 5 10

<210> SEQ ID NO 27
<211> LENGTH: 10
<212> TYPE: PRT
<213> ORGANISM: Artificial Sequence
<220> FEATURE:
<223> OTHER INFORMATION: One of the analogues of the native C-terminal decamer of OspC

<400> SEQUENCE: 27

Pro Val Val Ala Glu Ala Pro Lys Lys Pro
1 5 10

<210> SEQ ID NO 28
<211> LENGTH: 10
<212> TYPE: PRT
<213> ORGANISM: Artificial Sequence
<220> FEATURE:
<223> OTHER INFORMATION: One of the analogues of the native C-terminal decamer of OspC

<400> SEQUENCE: 28

-continued

Pro Val Val Ala Ala Ser Pro Lys Lys Pro
1 5 10

<210> SEQ ID NO 29
<211> LENGTH: 10
<212> TYPE: PRT
<213> ORGANISM: Artificial Sequence
<220> FEATURE:
<223> OTHER INFORMATION: One of the analogues of the native C-terminal decamer of OspC

<400> SEQUENCE: 29

Pro Val Val Phe Glu Ser Pro Lys Lys Pro
1 5 10

<210> SEQ ID NO 30
<211> LENGTH: 10
<212> TYPE: PRT
<213> ORGANISM: Artificial Sequence
<220> FEATURE:
<223> OTHER INFORMATION: One of the analogues of the native C-terminal decamer of OspC

<400> SEQUENCE: 30

Pro Val Ala Ala Glu Ser Pro Lys Lys Pro
1 5 10

<210> SEQ ID NO 31
<211> LENGTH: 10
<212> TYPE: PRT
<213> ORGANISM: Artificial Sequence
<220> FEATURE:
<223> OTHER INFORMATION: One of the analogues of the native C-terminal decamer of OspC

<400> SEQUENCE: 31

Pro Ala Val Ala Glu Ser Pro Lys Lys Pro
1 5 10

<210> SEQ ID NO 32
<211> LENGTH: 10
<212> TYPE: PRT
<213> ORGANISM: Artificial Sequence
<220> FEATURE:
<223> OTHER INFORMATION: One of the analogues of the native C-terminal decamer of OspC

<400> SEQUENCE: 32

Ala Val Val Ala Glu Ser Pro Lys Lys Pro
1 5 10

<210> SEQ ID NO 33
<211> LENGTH: 10
<212> TYPE: PRT
<213> ORGANISM: Artificial Sequence
<220> FEATURE:
<223> OTHER INFORMATION: One variant of the C-terminal decamer of OspC, wherein the carboxyl group was replaced by an amino group.
<220> FEATURE:
<221> NAME/KEY: misc_feature
<222> LOCATION: (10)..(10)
<223> OTHER INFORMATION: Pro is amidated

<400> SEQUENCE: 33

Pro Val Val Ala Glu Ser Pro Lys Lys Pro
1 5 10

-continued

<210> SEQ ID NO 34
<211> LENGTH: 10
<212> TYPE: PRT
<213> ORGANISM: Artificial Sequence
<220> FEATURE:
<223> OTHER INFORMATION: A substitution analog prepared to further elucidate the importance of single amino acid residues in the C-terminus of OspC
<220> FEATURE:
<221> NAME/KEY: misc_feature
<222> LOCATION: (9)..(9)
<223> OTHER INFORMATION: Xaa is L-hydroxyproline, 1,2,3,4-L-tetrahydroisoquinoline-3-carboxylic acid, L-thiazolidine-4-carboxylic acid, homoproline, or D-proline

<400> SEQUENCE: 34

Pro Val Val Ala Glu Ser Pro Lys Xaa Pro
1 5 10

<210> SEQ ID NO 35
<211> LENGTH: 10
<212> TYPE: PRT
<213> ORGANISM: Artificial Sequence
<220> FEATURE:
<223> OTHER INFORMATION: A substitution analog prepared to further elucidate the importance of single amino acid residues in the C-terminus of OspC
<220> FEATURE:
<221> NAME/KEY: misc_feature
<222> LOCATION: (7)..(7)
<223> OTHER INFORMATION: Xaa is L-diaminopropionic acid, diaminoacetic acid, L-diaminobutyric acid, L-ornithine, D-arginine, or D-lysine

<400> SEQUENCE: 35

Pro Val Val Ala Glu Ser Xaa Lys Lys Pro
1 5 10

<210> SEQ ID NO 36
<211> LENGTH: 4
<212> TYPE: PRT
<213> ORGANISM: Artificial Sequence
<220> FEATURE:
<223> OTHER INFORMATION: A substitution analog prepared to further elucidate the importance of single amino acid residues in the C-terminus of OspC
<220> FEATURE:
<221> NAME/KEY: misc_feature
<222> LOCATION: (1)..(1)
<223> OTHER INFORMATION: Xaa is L-indoline-2-carboxylic acid

<400> SEQUENCE: 36

Xaa Lys Lys Pro
1

<210> SEQ ID NO 37
<211> LENGTH: 10
<212> TYPE: PRT
<213> ORGANISM: Artificial Sequence
<220> FEATURE:
<223> OTHER INFORMATION: One of the analogues of OspC synthesized and tested in order to investigate whether a proline helix structure is an important feature of the epitopic region

<400> SEQUENCE: 37

Pro Val Val Pro Glu Ser Pro Lys Lys Pro
1 5 10

<210> SEQ ID NO 38
<211> LENGTH: 10
<212> TYPE: PRT

-continued

<213> ORGANISM: Artificial Sequence
<220> FEATURE:
<223> OTHER INFORMATION: One of the analogues of OspC synthesized and tested in order to investigate whether a proline helix structure is an important feature of the epitopic region

<400> SEQUENCE: 38

Pro Val Val Ala Glu Ser Pro Lys Asn Pro
1 5 10

<210> SEQ ID NO 39
<211> LENGTH: 10
<212> TYPE: PRT
<213> ORGANISM: Artificial Sequence
<220> FEATURE:
<223> OTHER INFORMATION: One of the analogues of OspC synthesized and tested in order to investigate whether a proline helix structure is an important feature of the epitopic region

<400> SEQUENCE: 39

Pro Pro Pro Pro Glu Ser Pro Lys Lys Pro
1 5 10

<210> SEQ ID NO 40
<211> LENGTH: 11
<212> TYPE: PRT
<213> ORGANISM: Artificial Sequence
<220> FEATURE:
<223> OTHER INFORMATION: Biotinylated synthetic peptide used in the indirect streptavidin ELISA for IgM antibodies against carboxy-terminal OspC deca-peptide
<220> FEATURE:
<221> NAME/KEY: misc_feature
<222> LOCATION: (1)..(1)
<223> OTHER INFORMATION: Xaa is 6-aminohexanoic acid

<400> SEQUENCE: 40

Xaa Pro Val Val Ala Glu Ser Pro Lys Lys Pro
1 5 10

<210> SEQ ID NO 41
<211> LENGTH: 5
<212> TYPE: PRT
<213> ORGANISM: Artificial Sequence
<220> FEATURE:
<223> OTHER INFORMATION: synthetically produced polypeptide fragment
<220> FEATURE:
<221> NAME/KEY: misc_feature
<222> LOCATION: (1)..(1)
<223> OTHER INFORMATION: Xaa can be any amino acid

<400> SEQUENCE: 41

Xaa Pro Lys Lys Pro
1 5

<210> SEQ ID NO 42
<211> LENGTH: 5
<212> TYPE: PRT
<213> ORGANISM: Artificial Sequence
<220> FEATURE:
<223> OTHER INFORMATION: synthetically produced polypeptide fragment

<400> SEQUENCE: 42

Ser Pro Lys Lys Pro
1 5

<210> SEQ ID NO 43
<211> LENGTH: 6
<212> TYPE: PRT

-continued

```
<213> ORGANISM: Artificial Sequence
<220> FEATURE:
<223> OTHER INFORMATION: synthetically produced polypeptide fragment

<400> SEQUENCE: 43

His His His His His His
1               5
```

What is claimed is:

1. A method for diagnosing the early stages of *Lyme borreliosis*, the method comprising contacting immunoglobulins or T-cells obtained from the subject with at least one immunological agent comprising a polypeptide fragment which has a length of at the most 60 amino acid residues and which contains carboxyterminally a peptide with the general formula I:

$A^5$-$A^4$-$A^3$-$A^2$-$A^1$ (SEQ ID NO: 41)

where $A^1$ designates a residue of proline;

$A^2$ designates a residue of lysine;

$A^3$ designates a residue of lysine;

$A^4$ designates a residue of proline; and $A^5$ designates residues of any amino acid, and subsequently detecting the degree, if any, of immunological reactivity between the immunoglobulins and the immunological agent or between the T-cells and the immunological agent, a immunological reaction being indicative of sensitization with OspC polypeptide from *Borrelia burgdorferi* sensu lato.

2. A method according to claim 1, wherein $A^5$ designates a residue of a non-charged amino acid.

3. A method according to claim 1, wherein $A^5$ designates a residue of an amino acid selected from the group consisting of serine, threonine, asparagine, and alanine.

4. A method according to claim 1, wherein the peptide of formula I is identical to SEQ ID NO: 21.

5. A method according to claim 1, wherein the polypeptide fragment has a length of at the most 10 amino acid residues.

6. A method according to claim 1, wherein the polypeptide fragment is identical to the peptide or identical to SEQ ID NO.: 18.

7. A method according to claim 1, wherein the immunological average sensitivity in detecting randomly selected antisera from patients suffering from early stage *Lyme borreliosis* is at least 85% of that achieved by using full-length recombinant OspC in an otherwise corresponding immunoassay.

8. A method according to claim 1, wherein the immunological average sensitivity in detecting randomly selected antisera from patients suffering from early stage *Lyme borreliosis* is at least 90%.

9. A method according to claim 1, wherein the immunological agent or the polypeptide fragment comprises at least two copies of the peptide.

10. A method according to claim 1, wherein at least two different immunological agents are used, wherein one of the immunological agents detects the presence of antibodies against the flagellum of *Borrelia burgdorferi* sensu lato.

11. A method according to claim 1, which is combined with at least one second assay which is diagnostic for previous sensitization with antigens of *Borrelia-burgdorferi* sensu lato.

12. A method according to claim 1, which is combined with at least one second assay which is diagnostic for previous sensitization with antigens of *Borrelia-burgdorferi* sensu lato wherein the at least one second assay is an assay for the presence of antibodies against the flagellum of *Borrelia-burgdorferi* sensu lato.

13. A method according to claim 1, which is carried out in vitro.

14. A method according to claim 1, wherein the immunological agent, in addition to the polypeptide fragment, comprises a moiety which enables covalent or non-covalent binding of the polypeptide fragment to a solid or semi-solid carrier, support or surface.

15. A method according to claim 1, wherein the immunological agent, in addition to the polypeptide fragment, comprises a moiety which enables covalent or non-covalent binding of the polypeptide fragment to a solid or semi-solid carrier, support or surface and the non-covalent binding to the carrier, support or surface is enabled by the moiety having affinity to a component attached to the carrier, support or surface.

16. A method according to claim 1, wherein the immunological agent is immobilized to the solid or semi-solid surface or carrier by means of covalent or non-covalent binding, either prior to or after the addition of the immunoglobulins.

17. A method according to claim 1, wherein the immunological agent is immobilized to a solid or semi-solid surface or carrier by means of covalent or non-covalent binding, either prior to or after the addition of the immunoglobulins, a solid or semi-solid surface or carrier is selected from the group consisting of a floor or wall in a microtiter well; a filter surface; a hollow fibre; a beaded chromatographic medium selected from an agarose or polyacrylamide gel; a magnetic bead; a fibrous cellulose matrix; an HPLC matrix; an FPLC matrix; a substance having molecules of such a size that the molecules with the immunological agent bound thereto, when dissolved or dispersed in a liquid phase, can be retained by means of a filter; a substance capable of forming micelles or participating in the formation of micelles allowing a liquid phase to be changed or exchanged without entraining the micelles; and a water-soluble polymer.

18. A method according to claim 1, wherein the immunological agent is provided with a detectable label.

19. A method according to claim 1, wherein the immunoglobulins are of IgM or of IgA type.

20. A method using a polypeptide fragment as defined in claim 1, for the manufacture of a diagnostic agent for diagnosis of diseases caused by *Borrelia burgdorferi* sensu lato.

21. A method according to claim 1, wherein at least two different immunological agents are used, the immunological agents differing in the amino acid sequence of the polypeptides fragment.

22. A method according to claim 1, wherein at least two different immunological agents are used, the immunological agents differing in the amino acid sequence of the peptide.

23. A method according to claim 1, wherein the degree of immunological reactivity is detected by means of an immunoassay selected from the group consisting of a direct or indirect EIA an immunoblot technique an RIA, and any other non-enzyme linked antibody binding assay.

24. A method according to claim 23, wherein said EIA is an ELISA, said immunoblot technique is a Western blot, an RIA, and said non-enzyme linked antibody binding assay is a fluorescence, agglutination or precipitation reaction, and nephelometry.

25. A method according to claim 1, wherein the degree of immunological reactivity is detected by means of an immunoassay selected from the group consisting of a direct or indirect EIA, an immunoblot technique, an RIA, and a non-enzyme linked antibody binding assay wherein the immunoassay comprises:

immobilizing immunoglobulins to be detected, adding the immunological agent and thereafter detecting the amount of immunological agent bound to the immunoglobulins, immobilizing the immunological agent, adding the immunoglobulins and thereafter detecting the amount of immunoglobulins bound to the immunological agent, or reacting the immunoglobulins and the immunological agent without any of the reactants being immobilized and subsequently detecting the amount of complexes of immunological agent and immunoglobulins.

26. A method for diagnosing the early stages of *Lyme borreliosis*, the method comprising contacting immunoglobulins or T-cells obtained from the subject with at least one immunological agent comprising a polypeptide fragment which has a length of at the most 60 amino acid residues and which contains carboxyterminally a peptide with the general formula I:

$A^5$-$A^4$-$A^3$-$A^2$-$A^1$ (SEQ ID NO: 42)

where $A^1$ designates a residue of proline;

$A^2$ designates a residue of Lysine;

$A^3$ designates a residue of Lysine;

$A^4$ designates a residue of Proline; and $A^5$ designates a Seine residues, and subsequently detecting the degree, if any, of immunological reactivity between the immunoglobulins and the immunological agent or between the T-cells and the immunological agent, a immunological reaction being indicative of sensitization with OspC polypeptide from *Borrelia burgdorferi* sensu lato.

27. The method according to 22, wherein said at least two different immunological agents are SEQ ID NO.:1 and SEQ ID NO.:37.

28. The method according to claim 15, wherein said moiety is a biotin or biotinyl group bound to an amino acid group of the polypeptide fragment and the component is avidin, streptavidin.

29. The method according to claim 27, wherein said biotin or biotinyl group is 6-aminohexanoic acid.

30. The method according to claim 15, wherein said moiety has the amino acid sequence His-His-His-His-His-His (SEQ ID NO.:43).

31. The method according to claim 18, wherein said detectable label is selected from the group consisting of a radioactive, an enzymatic, a fluorescent and avidin/biotin.

32. The method according to claim 25, wherein said immunoglobulins are detected by labeling said immunological agent or adding a labeled substance that specifically recognizes said immunological agent.

33. The method according to claim 25, wherein said immunological agent is detected by adding a labeled substance that specifically recognizes said immunoglobulins.

34. The method according to claim 25, wherein said complexes of immunological agent and immunoglobulins are detected by labeling the immunological agent or adding a labeled substance that specifically recognizes the immunological agent.

35. The method according to claim 1, wherein said immunological agent comprises SEQ ID NO.:1.

36. The method according to claim 1, wherein the polypeptide fragment has a length selected from the group consisting of 9, 8, 7, 6 and 5 amino acid residues.

37. The method for diagnosing the early stages of *Lyme borreliosis* according to claim 26, wherein the polypeptide fragment has a length of at the most 8 amino acid residues.

38. The method for diagnosing the early stages of *Lyme borreliosis* according to claim 1, wherein the polypeptide fragment has a length of at the most 9 amino acid residues.

39. A method for diagnosing the early stages of *Lyme borreliosis*, the method comprising contacting immunoglobulins or T-cells obtained from the subject with at least one immunological agent comprising a synthetically produced polypeptide fragment which has a length of at the most 60 amino acid residues and which contains carboxyterminally a peptide with the general formula I:

$A^5$-$A^4$-$A^3$-$A^2$-$A^1$ (SEQ ID NO:41)

where $A^1$ designates a residue of proline;

$A^2$ designates a residue of lysine;

$A^3$ designates a residue of lysine;

$A^4$ designates a residue of proline; and $A^5$ designates residues of any amino acid, and subsequently detecting the degree, if any, of immunological reactivity between the immunoglobulins and the immunological agent or between the T-cells and the immunological agent, a immunological reaction being indicative of sensitization with OspC polypeptide from *Borrelia burgdorferi* sensu lato.

40. A method for diagnosing the early stages of *Lyme borreliosis* according to claim 39, wherein synthetically produced polypeptide fragment has a length of at the most 9 amino acid residues.

41. The method according to claim 40, wherein $A^5$ designates a serine residue.

42. The method according to claim 39, wherein $A^5$ designates a serine residue.

43. The method according to claim 38, wherein $A^5$ designates a serine residue.

* * * * *